US011078222B2

(12) United States Patent
Martins Borges et al.

(10) Patent No.: US 11,078,222 B2
(45) Date of Patent: Aug. 3, 2021

(54) HYDROXYBENZOIC ACID DERIVATIVES, METHODS AND USES THEREOF

(71) Applicants: UNiVERSIDADE DO PORTO, Oporto (PT); CENTRO DE NEUROCIÊNCIAS E BIOLOGIA CELULAR, Coimbra (PT)

(72) Inventors: Maria Fernanda Martins Borges, Oporto (PT); Paulo Jorge Gouveia Simões Da Silva Oliveira, Coimbra (PT); José Carlos Santos Teixeira, Oporto (PT); Fernando Cagide Fagin, Oporto (PT); Ana Catarina Gomes Oliveira, Oporto (PT)

(73) Assignees: UNIVERSIDADE DO PORTO, Oporto (PT); CENTRO DE NEUROCIÊNCIAS E BIOLOGIA CELULAR, Coimbra (PT)

( * ) Notice: Subject to any disclaimer, the term of this patent is extended or adjusted under 35 U.S.C. 154(b) by 0 days.

(21) Appl. No.: 16/475,277

(22) PCT Filed: Dec. 29, 2017

(86) PCT No.: PCT/IB2017/058508
§ 371 (c)(1),
(2) Date: Jul. 1, 2019

(87) PCT Pub. No.: WO2018/122789
PCT Pub. Date: Jul. 5, 2018

(65) Prior Publication Data
US 2019/0330249 A1    Oct. 31, 2019

(30) Foreign Application Priority Data
Dec. 29, 2016  (PT) .......................................... 109818

(51) Int. Cl.
*C07F 9/54*         (2006.01)

(52) U.S. Cl.
CPC ................................. *C07F 9/5456* (2013.01)

(58) Field of Classification Search
CPC ....................................................... C07F 9/5456
See application file for complete search history.

(56) References Cited

U.S. PATENT DOCUMENTS

| 8,962,600 B2 * | 2/2015 | Kalyanaraman | A61P 25/14 514/107 |
| 9,963,474 B2 * | 5/2018 | Murphy | C07F 9/5442 |

FOREIGN PATENT DOCUMENTS

| WO | 2010126719 A1 | 11/2010 |
| WO | 2015075200 A1 | 5/2015 |

OTHER PUBLICATIONS

Smolii et al (1989) : STN International HCAPLUS database, (Columbus, Ohio), Accession No. 1989: 457663.*
Toure et al (1997): STN International HCAPLUS database, (Columbus, Ohio), Accession No. 1997: 205916.*
International Search Report and Written Opinion for International Patent Application No. PCT/IB2017/058508 dated Mar. 21, 2018; 8 pages.

* cited by examiner

*Primary Examiner* — Golam M Shameem
(74) *Attorney, Agent, or Firm* — Leason Ellis LLP

(57) ABSTRACT

The present disclosure relates to the design and synthesis of new mitochondriotropic antioxidant compounds based on hydroxybenzoic acids and analogues. Furthermore, this disclosure is also related to the methods and uses of the hydroxybenzoic based derivatives and analogues, for example, in the field of human and animal diseases, for instance to treat mitochondrial dysfunction or mitochondrial deficiencies, and cosmetics, for instance to prevent or delay skin aging.

18 Claims, 10 Drawing Sheets

A

B

A

B

HYDROXYBENZOIC ACID DERIVATIVES, METHODS AND USES THEREOF

CROSS-REFERENCE TO RELATED APPLICATIONS

This application is a U.S. National Stage Application under 35 U.S.C. § 371 of International Patent Application No. PCT/IB2017/058508, filed Dec. 29, 2017, which claims priority to Portugal Application No. 109818, filed Dec. 29, 2016, which are hereby incorporated by reference in their respective entireties.

TECHNICAL FIELD

The present disclosure is related to the design and synthesis of new mitochondriotropic antioxidant compounds based on hydroxybenzoic acids and analogues. Furthermore, this disclosure is also related to the methods and uses of the hydroxybenzoic based derivatives and analogues, for example, in the field of human and animal diseases, for instance to treat mitochondrial dysfunction or mitochondrial deficiencies, and cosmetics, for instance to prevent or delay skin aging.

BACKGROUND ART

Mitochondria play a vital role in regulating energy metabolism, cytosolic calcium concentration, ROS production, and cell death pathways. Excessive ROS production, if not counteracted by intrinsic defense mechanisms, can cause oxidative damage on cellular components such as lipids, proteins and nucleic acids, which lead to subsequent cell death by necrosis or apoptosis.

Mitochondrial alterations resulting from augmented oxidative stress play a crucial role in oxidative stress related diseases such as cancer, stroke, heart failure, obesity and neurodegenerative disorders[1]. Targeting mitochondria with organelle-specific drugs is believed to be an effective therapeutic strategy. More specifically, controlling the cellular ROS balance via selective delivery of an antioxidant to mitochondria has been described as an effective and promising therapeutic strategy for the prevention and/or treatment of oxidative stress-related diseases[2].

Although ROS production is tightly regulated by an endogenous antioxidant network, its overproduction can lead to mitochondrial oxidative damage and dysfunction. Mitochondrial oxidative dysfunction impairs multiple metabolic and signalling pathways and can trigger cell death via apoptosis or necrosis.

Oxidative stress and mitochondrial dysfunction have been associated to aging and several oxidative stress associated pathologies, for instance diabetes, non-alcoholic fatty liver disease, cardiovascular diseases, acute pancreatitis and neurodegenerative diseases, including Alzheimer or Parkinson disease, and amyotrophic lateral sclerosis. Thus, the prevention of mitochondrial oxidative damage is nowadays a recognized pharmacological strategy to delay disease progression.

In a pathological event, the pool of endogenous antioxidant defenses may not be enough to deal with the increased oxidant production so it has been suggested that the administration of exogenous antioxidants can be beneficial to decrease cell injury, given that they not only compensate the insufficiency of endogenous defense systems but also improve the overall antioxidant response. Exogenous antioxidants may in theory block the complex networks of oxidative damage pathways at different levels, yielding a therapeutic effect. Consequently, antioxidants that are exogenously acquired from diet may have important functions in redox cell homeostasis and can be important for cellular function and disease prevention.

While the role of mitochondria in disease pathogenesis is rather consensual, targeting that organelle to prevent disruption is not always straightforward. Improvement of mitochondrial function through prevention/minimization of oxidative damage is an effective and promising therapeutic strategy. Since maintaining ROS/antioxidant ratio and redox maintenance is critical for cell signalling targeting antioxidants to dysfunctional mitochondria is of pharmacologic interest.

A number of mitochondria-targeted antioxidants are being developed, in particular those using triphenylphosphonium (TPP) as carrier. This type of lipophilic cation can cross the mitochondrial membrane and accumulate within the mitochondrial matrix taking advantage of the inner membrane electric potential gradient[3-5].

One of the most studied mitochondria-targeted antioxidants is Mitoquinone (MitoQ, MitoQ10, [10-(4,5-dimethoxy-2-methyl-3,6-dioxo-1,4-cyclohexadien-1-yl)decyl] triphenylphosphonium methanesulfonate). MitoQ is constituted by an endogenous antioxidant moiety (coenzyme Q) covalently linked to a 10-carbon alkyl chain (dTPP) spacer and to a triphenylphosphonium (TPP) cation. MitoQ is under clinical trials for different pathological events, namely for hepatitis C. Yet, clinical trials using MitoQ as a therapeutic solution for neurodegenerative diseases have produced disappointing results[4,5].

Another relevant mitochondrial-targeted antioxidant is SKQ1 [10-(4,5-dimethyl-3,6-dioxocyclohexa-1,4-dien-1-yl) decyl)triphenylphosphonium bromide)], which is based on plastoquinone, a quinone involved in the electron transfer chain of chloroplasts. SkQ1 was shown to decrease oxidative stress inside mitochondria and to provide significant protecting benefits for dry-eye condition.

Nevertheless, there is still a need for more effective and safe mitochondrial modulators to be used in therapy and in other applications such as supplements or nutraceuticals and in cosmetic field.

Polyphenols are plant secondary metabolites generally involved in defense against oxidative stressors that are found largely in fruits, vegetables, cereals and beverages composing human diet. Their daily dietary intake in the conventional Western diet was estimated to be about 1 g. Epidemiological studies and associated meta-analyses strongly suggested an association between the consumption of polyphenol-rich diets and the prevention of oxidative stress related diseases, such as cancer, diabetes, cardiovascular and neurodegenerative diseases.

Hydroxybenzoic acids (HBAs), a phenolic acid subclass, comprise seven carbon atoms (C6-C1) connected to at least one hydroxyl group. Some HBA derivatives are currently used as food antioxidant additives to prevent or minimize the oxidation of nutrients and to maintain or improve food's nutritional value. Hydroxybenzoic acids and derivatives are also used as excipients in cosmetic and pharmaceutical industries due to their antioxidant properties. However, several drawbacks have been pointed out mainly related with their efficacy.

The antioxidant activity of HBAs has been associated with their chelating and free radical scavenging properties, namely by inhibiting lipid peroxidation processes. It is also currently recognized that HBAs derivatives can play a role in the inhibition of several pro-oxidant enzymes that are involved in reactive oxygen species (ROS) production. Scientific evidence pointed out that HBAs antioxidant efficacy is related to the number and position of hydroxyl groups located on the aromatic ring. These different mechanisms of action can result in an inhibition or reduction of ROS formation, interrupting the propagation of free radical chain reactions or delaying their start or reaction rates.

The usefulness of HBAs and their derivatives in therapy, alone or as adjuvants, is mainly limited due to bioavailability and druggability limitations. Despite their putative health promoting properties, the bioavailability of orally administered polyphenols appears insufficient to allow enough concentrations for systemic therapy, a problem that is mainly related with their physicochemical properties (e.g. lipophilicity) and extensive and rapid metabolism. Different strategies have been developed so far to increase the lipophilicity and stability of HBAs allowing for a better bioavailability and for improving their delivery to an intracellular target such as mitochondria.

These facts are disclosed in order to illustrate the technical problem addressed by the present disclosure.

General Description

Mitochondria are attractive targets for a number of molecules, which can minimize organelle damage in the context of different pathologies.

Increasing evidence suggests that mitochondrial dysfunction amplifies oxidative stress events playing a crucial role in different pathologies and aging process. Mitochondrial iron sulphur centers, membrane polyunsaturated fatty acids, proteins and mitochondrial DNA are susceptible to oxidative damage often leading to organelle and cellular disruption.

The present disclosure reports the design and synthesis of new mitochondriotropic antioxidants based on dietary hydroxybenzoic acids and analogues(AntiOxBENs).

As part of the present disclosure, which is related with the development of effective antioxidants based on natural models, it is herein reported the development of novel mitochondrial-directed antioxidant based on natural dietary HBAs, with robust antioxidant and iron-chelating properties, while maintaining low cytotoxicity profile.

The present disclosure relates to a compound of formula I

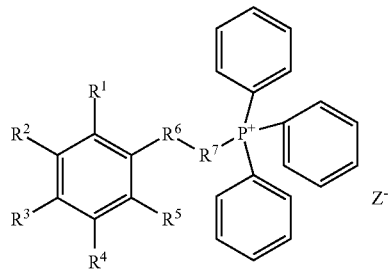

or a salt, solvate, hydrate, tautomer, stereoisomer; preferably a pharmaceutical acceptable salt, solvate, hydrate, tautomer, stereoisomer; for use in medicine, wherein
$R^1$, $R^2$, $R^3$, $R^4$, $R^5$, $R^6$ and $R^7$ are independently selected from each other;
$R^1$, $R^2$, $R^3$, $R^4$ and $R^5$ are selected from H, halogen, hydroxyl, methyl, methoxyl, amino, carboxylic acid, or nitro group;
$R^6$ is a secondary amide or tertiary amide;
$R^7$ is an alkyl chain, an alkenyl chain, an alkynyl chain, a substituted aryl or a secondary amide and
$Z^-$ is an acceptable anion, preferably an acceptable pharmaceutical anion, in particular a halogen, more in particular Cl.

The present disclosure also relates to a compound of formula I

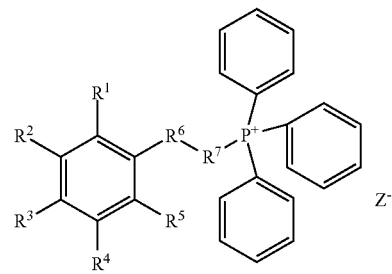

or a salt, solvate, hydrate, tautomer, stereoisomer; preferably a pharmaceutical acceptable salt, solvate, hydrate, tautomer, stereoisomer;
wherein
$R^1$, $R^2$, $R^3$, $R^4$, $R^5$, $R^6$ and $R^7$ are independently selected from each other;
$R^1$, $R^2$, $R^3$, $R^4$ and $R^5$ are selected from H, halogen, hydroxyl, methyl, methoxyl, amino, carboxylic acid, or nitro group;
$R^6$ is a secondary amide or tertiary amide;
$R^7$ is an alkyl chain, an alkenyl chain, an alkynyl chain, a substituted aryl or a secondary amide and
$Z^-$ is an acceptable anion, preferably an acceptable pharmaceutical anion, in particular a halogen, more in particular Cl;
with the proviso that

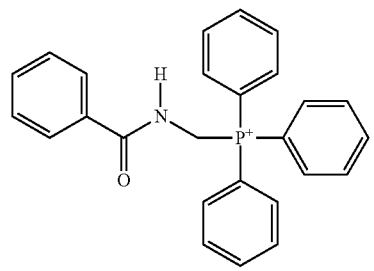 [SMILES: O=C(NC[P+](c1ccccc1)(c1ccccc1)c1ccccc1)c1ccccc1]

is excluded.

Based on the International Union of Pure and Applied Chemistry (IUPAC) definitions, an alkyl group is defined as a univalent group derived from alkanes by removal of a hydrogen atom from any carbon atom—$C^nH_{2n+1}$. The groups derived by removal of a hydrogen atom from a terminal carbon atom of unbranched alkanes form a subclass of normal alkyl (n-alkyl) groups $H(CH_2)_n$. The groups $RCH_2$, $R_2CH$ ($R \neq H$), and $R_3C$ ($R \neq H$) are primary, secondary and tertiary alkyl groups, respectively. An aryl group is derived from arenes (monocyclic and polycyclic aromatic hydrocarbons) by removal of a hydrogen atom from a ring carbon atom.

"Alkyl" includes "lower alkyl" and extends to cover carbon fragments having up to 30 carbon atoms. Examples of alkyl groups include octyl, nonyl, norbornyl, undecyl, dodecyl, tridecyl, tetradecyl, pentadecyl, eicosyl, 3,7-diethyl-2,2-dimethyl-4-propylnonyl, 2-(cyclododecyl)ethyl, adamantyl, and the like.

"Lower alkyl" means alkyl groups of from 1 to 7 carbon atoms. Examples of lower alkyl groups include methyl, ethyl, propyl, isopropyl, butyl, sec- and tert-butyl, pentyl, hexyl, heptyl, cyclopropyl, cyclobutyl, cyclopentyl, cyclohexyl, cycloheptyl, 2-methylcyclopropyl, cyclopropylmethyl, and the like.

In an embodiment, the compound of formula I is

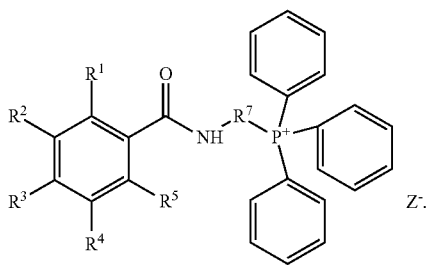

In an embodiment, the compound of formula I is

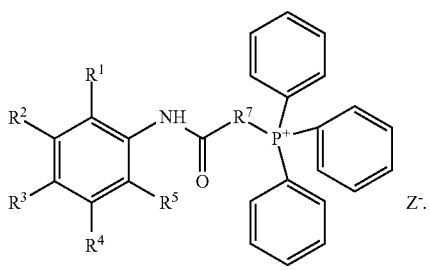

In an embodiment,
$R^7$ is a secondary amide of $R^8$—(C=O)NH—$R^9$ amide;
$R^8$ and $R^9$ are independently selected from each other and $R^8$ and $R^9$ are the alkyl chain, an alkenyl chain, an alkynyl chain or an substituted aryl.

In an embodiment, the substituted aryl is an alkane-aryl substituted, alkene-aryl substituted, or alkyne-aryl substituted.

In an embodiment, the alkane-aryl substituted, alkene-aryl substituted, or alkyne-aryl substituted is $C_1$-$C_6$-alkyl, $C_3$-$C_8$-cycloalkyl, $C_6$-$C_{10}$-aryl, $C_6$-$C_{10}$-aryl-$C_1$-$C_5$-alkyl, $C_1$-$C_6$-alkoxy, $C_6$-$C_{10}$-aryloxy, $C_6$-$C_{10}$-aryl-$C_1$-$C_8$-alkoxy, hydroxyl, $CO_2H$, $C_1$-$C_6$-alkoxycarbonyl, $C_6$-$C_{10}$-aryloxycarbonyl, $C_6$-$C_{10}$-aryl-$C_1$-$C_8$-alkoxycarbonyl, $C_1$-$C_6$-alkylcarbonyl, $C_6$-$C_{10}$-arylcarbonyl, $C_6$-$C_{10}$-aryl-C1-C8-alkylcarbonyl, $C_1$-$C_6$-alkylcarboxy, $C_6$-$C_{10}$-arylcarboxy, $C_1$-$C_6$-alkylmercaptyl, $C_6$-$C_{10}$-arylmercaptyl, $C_1$-$C_6$-alkylmercaptocarbonyl, $C_3$-$C_8$-cycloalkylmercaptocarbonyl, $C_6$-$C_{10}$-aryl mercaptocarbonyl, $C_1$-$C_6$-alkylmercaptocarboxy, $C_6$-$C_{10}$-arylmercaptocarboxy, $C_1$-$C_6$-alkylsulfonyl, $C_6$-$C_{10}$-arylsulfonyl, $C_1$-$C_6$-alkylsulfoxy, $C_6$-$C_{10}$-arylsulfoxy;

each of which is substituted once or several times by $C_1$-$C_6$-alkyl, $C_1$-$C_6$-alkoxy, COOH; $CONH_2$, substituted once or twice with $C_1$-$C_6$-alkyl; $SO_3H$, amino, thiol, hydroxyl, nitro, cyano, fluoro, chloro, bromo, iodo, $CF_3$ or $OCF_3$;

wherein several of these optional substituents are combined to form anellated saturated, unsaturated or aromatic homo- or hetero-ring systems; or a saturated, unsaturated or aromatic heterocycle substituted once or several times by $C_1$-$C_6$-alkyl, $C_1$-$C_6$-alkoxy, COOH; $CONH_2$, substituted once or twice.

In an embodiment, the alkyl chain, the alkenyl chain or the alkynyl chain is a $C_1$-$C_{30}$ chain, preferably $C_1$-$C_{18}$ chain.

In an embodiment, the alkyl chain, the alkenyl chain or the alkynyl chain is a $C_2$-$C_{16}$ chain, preferably a $C_3$-$C_{16}$ chain, more preferably a $C_5$-$C_{14}$ chain, even more preferably $C_6$-$C_{14}$.

In an embodiment, the alkyl chain is a $C_5$ alkyl chain, $C_6$ alkyl chain, a $C_7$ alkyl chain, a $C_8$ alkyl chain, a $C_9$ alkyl chain, a $C_{10}$ alkyl chain, a $C_{11}$ alkyl chain, a $C_{12}$ alkyl chain, a $C_{13}$ alkyl chain, or a $C_{14}$ alkyl chain.

In an embodiment, $R^1$ and $R^5$ are H.
In an embodiment, $R^2$ and $R^3$ are OH.
In an embodiment, $R^4$ is H or OH.
In an embodiment, $R^7$ is the $C_6$ alkyl chain.
In an embodiment, $R^8$ and $R^9$ are independently of each other the $C_5$ alkyl chain or the $C_6$ alkyl chain.
In an embodiment, the halogen is F, Cl, Br, I or At.
In an embodiment, the compound is 6-(3,4-dihydroxybenzamido)hexyltriphenylphosphonium bromide.
In an embodiment, the compound is 6-(3,4,5-trihydroxybenzamido)hexyltriphenylphosphonium bromide.
In an embodiment, the compound is 5-(6-(3,4,5-trihydroxybenzamido)hexylamino) carbonylpentyl]triphenylphosphonium bromide.

The present disclosure also relates to any compound, or related ones, now disclosed for use in medicine, veterinary or cosmetic.

In an embodiment, the disclosed compounds, or related ones, may be used for modulating at least one of mitochondrial morphology and/or expression of OXPHOS enzymes.

In an embodiment, the disclosed compounds, or related ones, may be used for the treatment or prevention or suppression of symptoms associated with a mitochondrial disorder or with a condition associated with mitochondrial dysfunction in general, including diseases originated from mitochondrial respiratory chain defects.

In an embodiment, the mitochondrial disorder is a disorder selected from the group consisting of: Myoclonic epilepsy; Myoclonic Epilepsy with Ragged Red Fibers; Leber's Hereditary Optic Neuropathy; neuropathy ataxia and retinitis pigmentosa; Mitochondrial Myopathy, Encephalopathy, Lactacidosis, Stroke; Leigh syndrome; Leigh-like syndrome; Dominant Optic atrophy; Kearns-Sayre Syndrome; Maternally Inherited Diabetes and Deafness; Alpers-Huttenlocher syndrome; Ataxia Neuropathy spectrum; Chronic Progressive External Ophthalmoplegia; Pearson syndrome; Mitochondrial Neuro-Gastro-Intestinal Encephalopathy; Sengers syndrome; 3-methylglutaconic aciduria, sensorineural deafness, encephalopathy and neuroradiological findings of Leigh-like syndrome; myopathy; mitochondrial myopathy; cardiomyopathy; and encephalomyopathy, deficient Leigh syndrome due to complex IV surfeit protein deficiency; isolated or combined OXPHOS deficiencies with so far unsolved genetic defect including disturbed pyruvate oxidation and ATP plus PCR production rates.

In an embodiment, the condition associated with mitochondrial dysfunction is a condition selected from the group consisting of: Friedreich's Ataxia; renal tubular acidosis; Parkinson's disease; Alzheimer's disease; amyotrophic lateral sclerosis; Huntington's disease; developmental pervasive disorders; hearing loss; deafness; diabetes; ageing; and adverse drug effects hampering mitochondrial function.

In an embodiment, the compounds now disclosed, or related ones, may be for use in the treatment or prevention or suppression of a neurodegenerative disease, non-alcoholic fatty liver disease, neoplasia, cancer, kidney disease, scleroderma, hepatic iron overload disease, hepatic copper overload disease, alopecia, human infertility, acute pancreatitis, fibromyalgia, mitochondrial disorder, or a condition associated with mitochondrial dysfunction or mitochondrial diseases.

In an embodiment, the compounds now disclosed, or related ones, may be for use in the treatment or prevention of neurodegenerative disease in particular for amyotrophic lateral sclerosis.

In an embodiment, the compounds now disclosed, or related ones, may be used for the treatment or prevention of cancer wherein the cancer is liver cancer, pancreatic cancer or biliary cancer.

In an embodiment, the compounds now disclosed, or related ones, may be for use in the treatment or prevention of non-alcoholic fatty liver disease wherein the non-alcoholic fatty liver disease is non-alcoholic fatty liver disease, non-alcoholic steatohepatitis, or hepatic cirrhosis.

In an embodiment, the compounds now disclosed, or related ones, may be for use in the treatment or prevention of kidney disease wherein the kidney disease is kidney cancer or kidney failure.

In an embodiment, the neoplasia disease may be cancer, in particular basal cell carcinoma, bone cancer, bowel cancer, brain cancer, breast cancer, cervical cancer, leukemia, liver cancer, lung cancer, lymphoma, melanoma, ovarian cancer, pancreatic cancer, prostate cancer, thyroid cancer or biliary cancer.

In an embodiment, the compounds now disclosed, or related ones, may be for use as antimicrobial agent, in particular as a disinfectant.

In an embodiment, the compounds now disclosed, or related ones, may be for use in a maintenance of a pluripotent cell culture, as a supplement for cell culture in particular as growth medium compound.

This disclosure also relates to a cell culture medium for maintaining pluripotent stem cells in an undifferentiated state comprising any of the compounds, or related ones, now disclosed.

In an embodiment, the compounds now disclosed, or related ones, may be for use as a muscle protector or muscle recovery after physical exercise.

In an embodiment, the compounds now disclosed, or related ones, may be for use as a cosmetic, or a supplement, or a nutraceutical, namely an anti-aging or as an anti-wrinkle skin care product.

In an embodiment, the compounds now disclosed, or related ones, may be for use as a probe in imaging studies, in particular to monitor mitochondrial imaging studies.

This disclosure also relates to a composition, preferably a pharmaceutical or cosmetic composition, comprising any of the compounds, or related ones, now disclosed and one or more pharmaceutically acceptable carriers, adjuvants, excipients, diluents, or mixtures thereof.

In an embodiment, the acceptable carrier may be selected from the following list: saline, gum acacia, gelatin, starch paste, talc, keratin, colloidal silica, urea, among others, or mixtures thereof.

In an embodiment, the adjuvant may be selected from the following list: oil-in-water emulsion adjuvant, aluminium adjuvant, a TLR-4 ligand, a saponin, among others, and mixtures thereof.

In an embodiment, the excipient may be selected from the following list: glucose, lactose, sucrose, glycerol monostearate, sodium chloride, glycerol, propylene, glycol, water, ethanol, among others, or mixtures thereof.

In an embodiment, the pharmaceutical composition may be administrated, as an example, via oral, parenteral, inhalational or topical. In the case of non-pharmaceutical composition, namely cosmetic compositions, the preferred route is topical.

In an embodiment, preferred pharmaceutical routes of administration include, but are not limited to, oral, parenteral, intramuscular, intravenous, in situ injection, intranasal, sublingual, intratracheal, and inhalation or topical.

In an embodiment, the pharmaceutical composition may be for use, for example, in a method for the treatment or prevention of a neurodegenerative disease, non-alcoholic fatty liver disease, neoplasia, kidney disease, scleroderma, hepatic iron overload disease, hepatic copper overload disease, alopecia, human infertility, acute pancreatitis or fibromyalgia, wherein the pharmaceutical composition is administered in a daily dose.

In an embodiment, the daily dose of the pharmaceutical composition may be 20 mg/day or 10 mg/day, among others.

In some embodiments, the dose or dosage form may be administered to the subject, for example, once a day, twice a day, or three times a day. In other embodiments, the dose is administered to the subject once a week, once a month, once every two months, four times a year, three times a year, twice a year, or once a year.

In an embodiment, the composition may comprise the one or more of the compounds disclosed, or related ones, in the present subject-matter, in an amount effective to improve the efficacy of other therapies, including immunotherapy or any pharmacological approach, by at least 5%, at least 10%, at least 15%, at least 20%, at least 25%, at least 30%, at least 40%, at least 50%, at least 60%, at least 70%, at least 75%, at least 80%, at least 90%, at least 95%, at least 95.7%, at least 98%, or at least 99% in the subject.

In some embodiments, the composition comprises a dose of 0.1-1000 mg. For example, in some embodiments, the preparation comprises a dose of 0.1 mg/kg, 0.2 mg/kg, 0.3 mg/kg, 0.4 mg/kg, 0.5 mg/kg, 0.7 mg/kg, 0.8 mg/kg, 0.9 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 25 mg/kg, 30 mg/kg, 40 mg/kg, 50 mg/kg, 60 mg/kg, 70 mg/kg, 80 mg/kg, 90 mg/kg, 100 mg/kg, 200 mg/kg, 250 mg/kg, 300 mg/kg, 400 mg/kg, 500 mg/kg, 600 mg/kg, 700 mg/kg, 750 mg/kg, 800 mg/kg, 900 mg/kg, or 1000 mg/kg. In some embodiments, the composition comprises a dose of 0.1-10 mg/kg, 0.1-100 mg/kg, 1-10 mg/kg, 1-100 mg/kg, 1-1000 mg/kg, 10-100 mg/kg, 10-1000 mg/kg, 100-1000 mg/kg, 10-50 mg/kg, 10-25 mg/kg, 10-20 mg/kg, 50-100 mg/kg, or 100-250 mg/kg.

This disclosure also provides a nanocarrier, for instance liposomes, wherein the nanocarrier comprise the compounds, or related ones, or the composition, now disclosed.

Throughout the description and claims the word "comprise" and variations of the word, are not intended to exclude other technical features, additives, components, or steps.

Additional objectives, advantages and features of the solution now disclosed will become apparent to those skilled in the art upon examination of the description or may be learned by practice of the solution.

Throughout the description and claims the word "comprise" and variations of the word, are not intended to exclude other technical features, additives, components, or steps. Additional objectives, advantages and features of the disclosure will become apparent to those skilled in the art upon examination of the description or may be learned by practice of the disclosure.

BRIEF DESCRIPTION OF THE DRAWINGS

The following figures provide preferred embodiments for illustrating the description and should not be seen as limiting the scope of present disclosure.

DETAILED DESCRIPTION

In an embodiment, and as an example, the synthetic strategies pursued for the development of a number of hydroxybenzoic acid derivatives (AntiOxBENs) are depicted in FIG. 1.

Figure 1A:
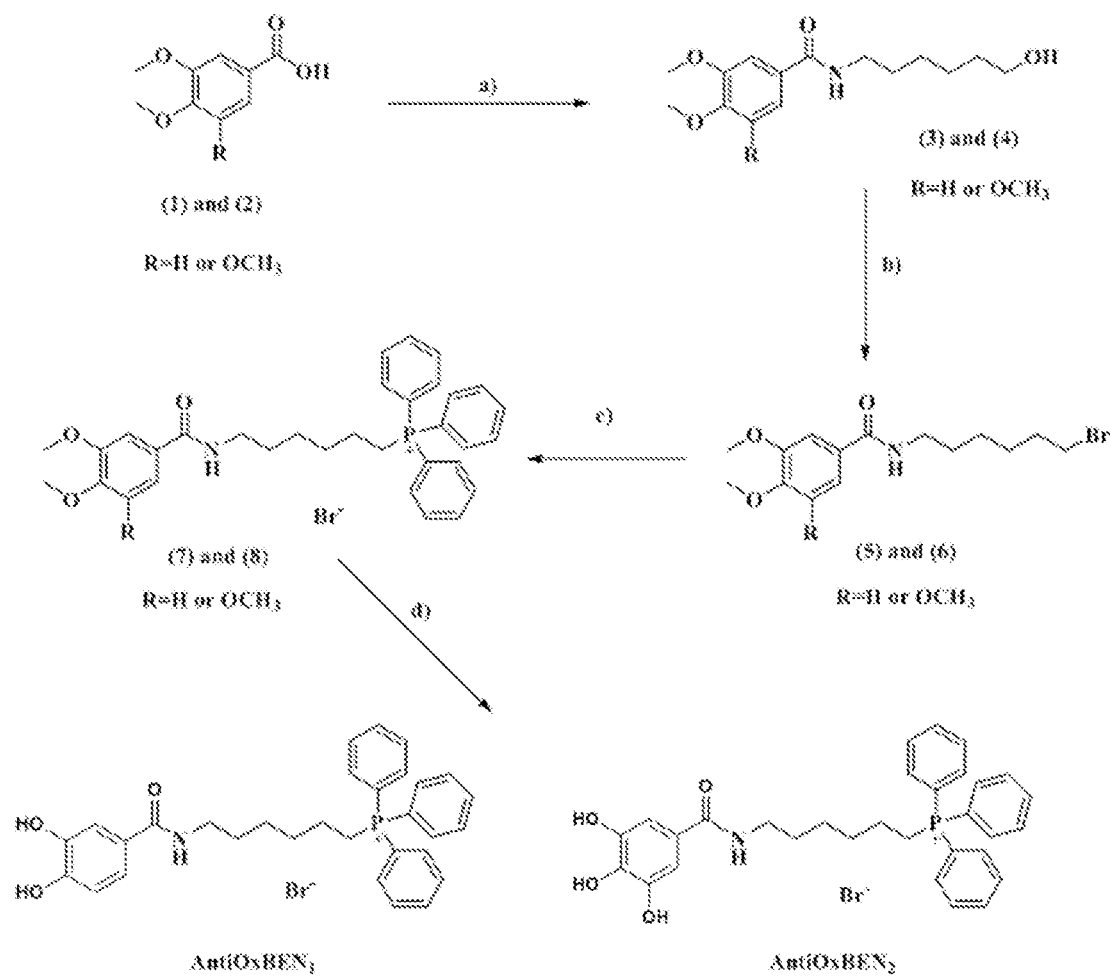
FIG. 1: Synthetic strategies pursued for the development of a number of mitochondriotropic antioxidants A—AntiOxBEN$_1$ and AntiOxBEN$_2$; B— AntiOxBEN3.

In an embodiment, and as an example, the mitochondriotropic antioxidants AntiOxBEN$_1$ and AntiOxBEN$_2$ were obtained following a four step synthetic strategy depicted in FIG. 1A. In this example, the starting materials di (1) or trimethoxybenzoic (2) acids were linked to a bifunctionalized alkyl spacer (6-aminohexan-1-ol) by an amidation reaction, using ethylchloroformate as coupling reagent. The second step reaction was aimed to convert the alcohol function (compounds 3 or 4) into a halide which is a good leaving group. The desired compounds (5 or 6) were attained in high yields, in particular 70-90%, by Appel modified reaction using 1,2-bis(diphenylphosphino)ethane (diphos). In a third step the triphenylphosphonium salts (compounds 7 or 8) were obtained via a SN2 reaction displaced by triphenylphosphine (PPh3). The synthesis of the hydroxylated analogues (AntiOxBEN$_1$ and AntiOxBEN$_2$) was performed by a demethylation process using boron tribromide ($BBr_3$).

In an embodiment, and as an example, the mitochondriotropic antioxidant AntiOxBEN$_3$ was obtained following a four step synthetic strategy depicted in FIG. 1B, in which trimethoxybenzoic acid (2) was linked to a monoprotected diamine spacer to obtain the derivative 9 that was subsequently deprotected in acid medium to obtain compound 10. Amine 10 was then coupled to the triphenylphosphonium cationic compound 11 by an amidation reaction in which the acylating agent was generated in situ. Then, compound 12 was demethylated using tribromide ($BBr_3$) solution to obtain AntiOxBEN$_3$. Globally, good to moderate yields have been obtained.

In an embodiment, and as an example, the AntiOxBENs antioxidant and redox properties were reported. Protocatechuic and gallic acids were also included in the study. Vitamin E and trolox were used as standards.

In an embodiment, the AntiOxBENs antioxidant ranking activity hierarchy was established by in vitro non-cell methods. The selected total antioxidant capacity (TAC) assays (DPPH, ABTS and GO) involved the spectrophotometric measurement of the radical absorbance decrease as a result of an in situ radical deactivation by an antioxidant. Compounds with higher antioxidant activity display lower $IC_{50}$ values. The results are depicted in Table 1.

The antioxidant data allow concluding that AntiOxBENs are effective antioxidants and that the attained $IC_{50}$ values followed the same trend in the three different assays. From the data attained it is possible to conclude that compounds with the pyrogallol moiety, in particular AntiOxBEN$_2$ and AntiOxBEN$_3$ displayed a superior antioxidant activity than catechol systems, in particular AntiOxBEN$_1$. In general, the introduction of the triphenylphosphonium (TPP) aliphatic side chain led to a slight decrease in the antioxidant activity, when compared to protocatechuic and gallic acids.

TABLE 1

Antioxidant activity and redox potentials (Ep) of mitochondria-targeted benzoic antioxidants.

| Compound | MW (gmol$^{-1}$) | $IC_{50}$ (µM) DPPH$^•$ | $IC_{50}$ (µM) ABTS$^{•+}$ | | $E_p$ (V) GO$^•$ |
|---|---|---|---|---|---|
| Protocatechuic acid | 154.12 | 27.6 | 30.1 | 5.8 | 0.257 |
| Gallic acid | 170.12 | 9.9 | 7.8 | 2.5 | 0.163 |
| MitoBEN$_1$ | 578.48 | 27.3 | 29.9 | 4.3 | 0.224 |
| MitoBEN$_2$ | 594.48 | 18.3 | 10.3 | 3.0 | 0.168 |
| MitoBEN$_3$ | 707.63 | 18.7 | 9.6 | 3.4 | 0.164 |
| Vitamin E | 430.71 | 26.3 | 30.9 | 5.8 | — |
| Trolox | 250.29 | 26.8 | 31.1 | 4.5 | 0.099 |

In an embodiment, and as an example, AntiOxBENs redox properties were evaluated (Table 1). Redox potentials are correlated with the ability of an antioxidant to donate a hydrogen atom and/or an electron to a free radical. Generally, low oxidation potentials (Ep) are associated with a superior antioxidant performance.

In an embodiment, the oxidative behaviour of the parent antioxidants (protocatechuic and gallic acids) and AntiOxBENs was evaluated at physiological pH 7.4, by differential pulse and cyclic voltammetry, using a glassy carbon working electrode. The redox data allow concluding that protocatechuic acid and AntiOxBEN$_1$ showed redox potentials (Ep) characteristic of the presence of a catechol group (Ep=0.257 and 0.224 V, respectively) (Table 1). For pyrogallol derivatives (gallic acid, AntiOxBEN$_2$, AntiOxBEN$_3$), a significant decrease in redox potentials was observed (Ep=0.163-0.168 V) (Table 1).

In an embodiment, only one anodic wave was observed in the differential pulse voltammetric study of the mitochondriotropic antioxidant AntiOxBEN$_1$. The occurrence of a single voltammetric wave seems to indicate AntiOxBEN$_1$ lower propensity to adsorb on the electrode surface, when compared to the parent acid. The differential pulse voltammetric study of gallic acid and its derivatives (AntiOxBEN$_2$ and AntiOxBEN$_3$) revealed the presence of two well-defined anodic waves at physiological pH. The oxidation peaks are related to the oxidation of the pyrogallol unit present in their structure.

In an embodiment, the cyclic voltammograms obtained for both protocatechuic acid and AntiOxBEN1 shows one anodic and the corresponding cathodic peak. The difference between anodic and cathodic peak potential value indicate an irreversible electron-transfer process. Cyclic voltammetric experiments presented a single oxidation peak with no distinct reduction wave on the reverse sweep, showing that gallic acid and AntiOxBEN$_2$ and AntiOxBEN$_3$ were also irreversibly oxidized.

In an embodiment, the obtained results allow concluding that gallic acid and AntiOxBEN$_2$ and AntiOxBEN$_3$ exhibited lower redox potentials than those observed for protocatechuic acid and AntiOxBEN$_1$ The decrease in the oxidation potential appears to be due to the existence of an additional phenolic group in gallic acid and its derivatives (pyrogallol unit). The extra hydroxyl group promote the stabilization of the radical intermediate produced by oxidation, which was translated into a substantial decrease of the redox potential obtained.

In an embodiment, the introduction of a triphenylphosphonium cation side chain does not have a noteworthy influence on the redox potentials obtained for AntiOxBENs. The data obtained suggest that the structural modifications performed result in modest or even no effect on the electron density of the catechol or pyrogallol ring.

In an embodiment, the data attained with TAC assays is consistent with AntiOxBENs redox outline. Overall the results reinforce the assumption that the number of hydroxyl substituents present on the benzoic aromatic ring is directly related with the antioxidant and electrochemical properties.

In an embodiment, and as an example, the AntiOxBEN$_1$ and AntiOxBEN$_2$ lipophilic properties were evaluated using differential pulse voltammetry (DPV) at physiological pH. The used technique is often used to mimic the transfer of ionic drugs through biological membranes as the process occurs at the interface between two immiscible electrolyte solutions (ITIES). The transfer potential ($E_{tr}$) at which the ionic drug, initially present in the aqueous phase (C=0.32 mM), is transferred to 1,6-dichlorohexane (DCH) phase is measured by differential pulse voltammetry (DPV). In the ITIES model, the transfer potential (Etr) becomes less positive with the increasing of the drug lipophilic character.

In an embodiment, and as an example, the AntiOxBEN$_1$ and AntiOxBEN$_2$ transfer potentials (Etr) was 0.405 V and 0.495 V, respectively. From the data it was concluded that the presence of an extra OH function in AntiOxBEN$_2$ (mitochondria-targeted antioxidant based on gallic acid) increased hydrophilicity in comparison with AntiOxBEN$_1$ (mitochondria-targeted antioxidant based on protocatechuic acid), which was translated in a rise of the transfer potential. As expected, due to their hydrophilicity hydroxybenzoic acids do not permeate.

In an embodiment, and as an example, AntiOxBENs chelating properties, namely their ability to chelate iron, were determined. Iron is a redox active metal that can catalyse Fenton and Haber-Weiss reactions generating hydroxyl radicals (.OH), which is a strong oxidant species that is linked with oxidative damage events with severe implications for human health and disease. To note that loss of mitochondrial iron homeostasis and consequent iron overload can contribute to mitochondrial dysfunction and in turn to different pathologies. So, the use of metal chelating agents, or antioxidants that operate by this or more than one mechanism can function as a therapeutic approach to prevent metal induced toxicity. Phenolic antioxidants that can operate by a combination of different mechanisms of action, namely by scavenging deleterious reactive species, by hydrogen donation and/or electron transference, and/or by chelation of pro-oxidant transition metals (namely Cu and Fe) can be of the utmost significance.

Figure 2:
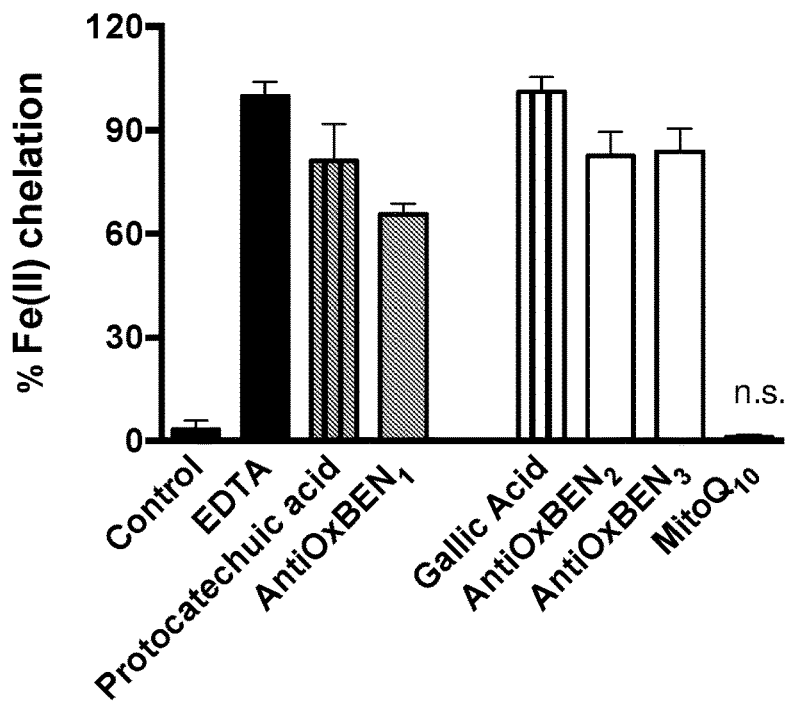
FIG. 2: Evaluation of iron chelating properties of benzoic acids and derivatives (AntiOxBEN$_1$, AntiOxBEN$_2$ and AntiOxBEN$_3$) and MitoQ. EDTA (chelating agent) was used as reference. Statistically significant compared with control group using one-way ANOVA (P<0.0001, n.s., not significant).

In an embodiment, the iron (II) chelation capacity of the novel AntiOxBENs was evaluated by the ferrozine assay using EDTA (ethylenediaminetetracetic acid) as reference. The iron chelating properties of protocatechuic and gallic acids, and MitoQ, a mitochondriotropic antioxidant, were also evaluated (FIG. 2). EDTA was able to chelate all the iron available in solution as it can inhibit completely the formation of the colored ferrozine-fe(II) complex.

In an embodiment, AntiOxBENs (catechol or pyrogallol series) and hydroxybenzoic acids, in opposition to MitoQ, were able to chelate ferrous iron (FIG. 2). Hydroxybenzoic acids (protocatechuic and gallic acids) were able to chelate iron efficiently; however, those presenting a pyrogallol moiety were more effective. AntiOxBENs (catechol or pyrogallol series) were also able to chelate ferrous iron, being those presenting a pyrogallol moiety more effective. The chelating properties of AntiOxBENs seem to be to some extent affected by the introduction of TPP cation spacer, when compared with the respective precursors. Yet, AntiOxBEN$_2$ and AntiOxBEN$_3$ were able to chelate more than 80% of the total iron present in solution.

In an embodiment, and facing the potent antioxidant capacity and the iron-chelating property of AntiOxBENs it is predicted that these innovative antioxidants may lead, after a drug discovery optimization program, to a drug candidate that can be applied to mitigate the effects of mitochondrial iron overload and/or reduce mitochondrial iron stores in oxidative stress related diseases and conditions.

Figure 3:
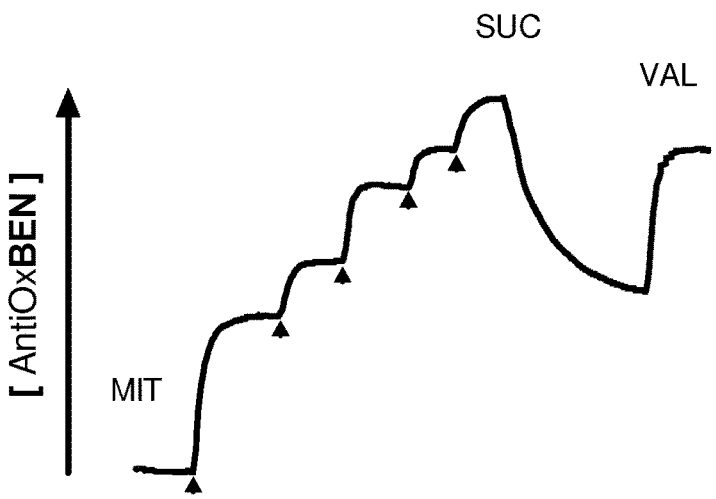
FIG. 3: (A) AntiOxBENs uptake by energised rat liver mitochondria measured using a TPP-selective electrode. (B) AntiOxBENs accumulation ratio by rat liver mitochondria. MIT, mitochondria; SUC, succinate; VAL, valinomicin.

In an embodiment, and as an example, the mitochondrial uptake of some AntiOxBENs was assessed in isolated rat liver mitochondria (RLM) in response to the membrane potential. AntiOxBENs can accumulate inside mitochondria driven by the Δψ (FIG. 3A). Different AntiOxBENs accumulation outlines within the mitochondrial matrix have been measured. The process was found to be related with the increment of the spacer length and aromatic substitution pattern (FIG. 3B). The small accumulation ratio observed for pyrogallol derivative AntiOxBEN$_2$ was significantly ameliorated by the increment of the spacer length. The following ranking order was attained: AntiOxBEN$_2$<AntiOxBEN$_1$<AntiOxBEN$_3$. All AntiOxBENs present an accumulation ratio comparable to that of MitoQ (FIG. 3B).

Mitochondrial membranes possess a high concentration of polyunsaturated fatty acids that are particularly prone to oxidation as they are located near to ROS producing sites.

In an embodiment, and as an example, AntiOxBENs antioxidant performance, on the protection of lipid peroxidation of RLM membranes was determined. Two different oxidative stressor agents, FeSO$_4$/H$_2$O$_2$/ascorbate and ADP/FeSO$_4$, and two end-points, TBARS production and oxygen-consumption, respectively, have been used. MitoQ was used as reference (FIGS. 4 and 5).

Figure 4:
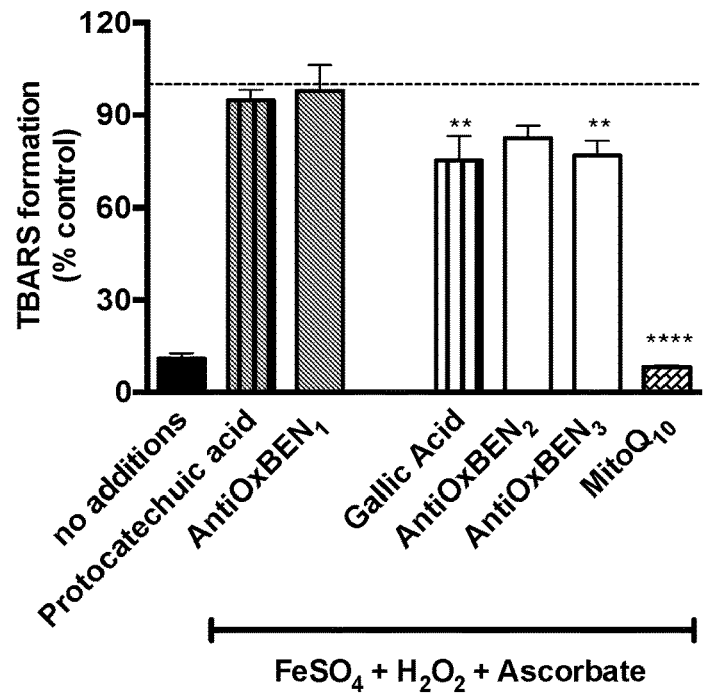
FIG. 4: Effect of benzoic acids, AntiOxBENs and MitoQ on mitochondrial lipid peroxidation under different oxidative conditions: (A) TBARS levels and (B) changes on oxygen consumption. The comparisons between control vs. AntiOxClNs (5 µM) pre-incubations were performed by using one-way ANOVA.
Figure 4:
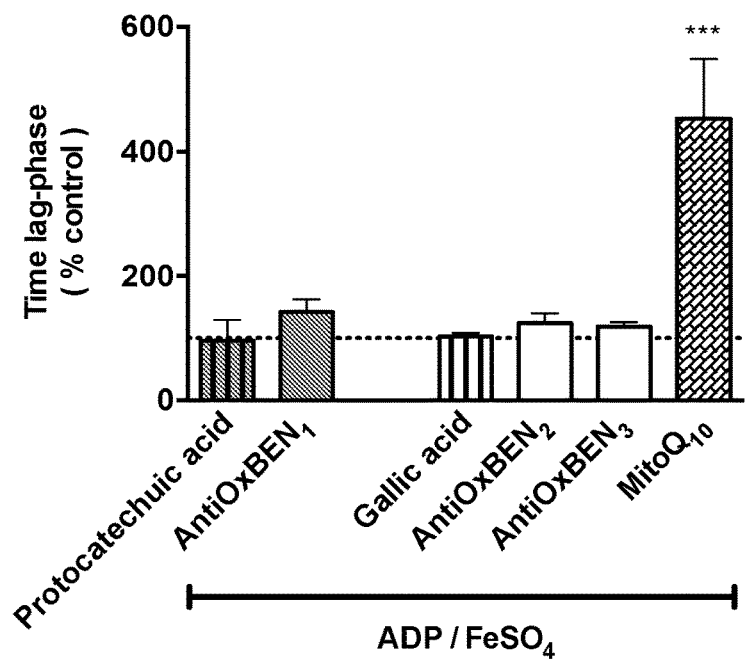
Figure 5:
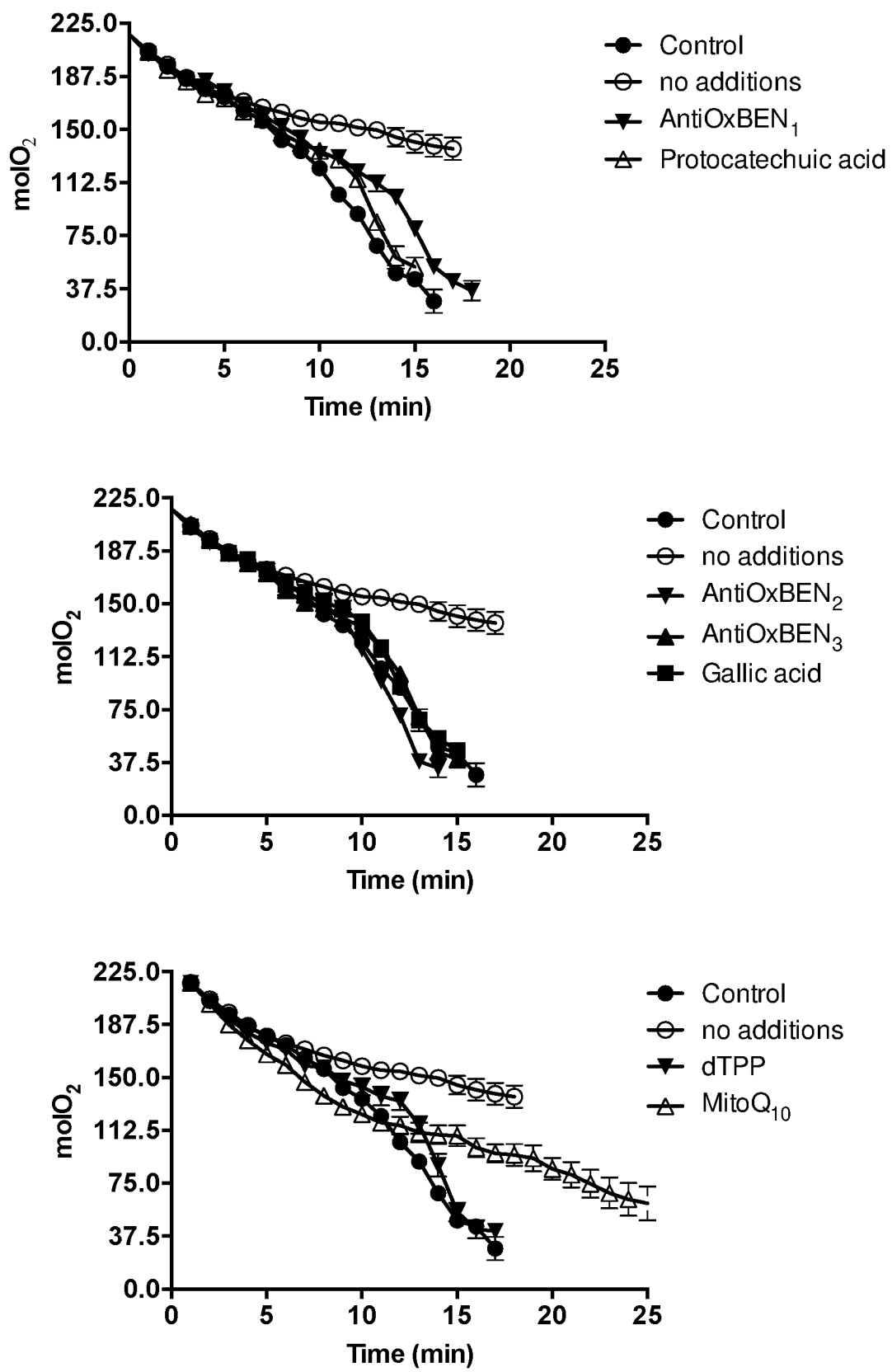
FIG. 5: Typical recording of the effect of benzoic acid and AntiOxBEN derivatives, containing a (A) catechol (protocatechuic acid and AntiOxBEN1) or (B) pyrogallol (gallic acid, AntiOxBEN2 and AntiOxBEN3) core and (C) dTPP and MitoQ on lipid peroxidation of RLM membranes induced by ADP and Fe' followed by oxygen consumption.

In an embodiment, gallic acid, AntiOxBEN$_2$ and AntiOxBEN$_3$, in FeSO$_4$/H$_2$O$_2$/ascorbate assay, were the most effective mitochondriotropic benzoic derivatives in preventing mitochondria lipid peroxidation (FIG. 4A). AntiOxBEN$_1$ and protocatechuic acid were not effective in preventing TBARS formation in RLM (FIG. 4A). In ADP/FeSO$_4$ assay, none of AntiOxBENs efficiently prevented lipid peroxidation (FIGS. 4B and 5). The ability of AntiOxBENs vs MitoQ to inhibit lipid peroxidation in RLM decreased in the order MitoQ>> AntiOxBEN$_3$≈gallic acid≈AntiOxBEN$_2$> AntiOxBEN$_1$≈protocatechuic acid. In general, pyrogallol-based AntiOxBENs (FIGS. 4 and 5) were more effective in delaying lipid peroxidation membrane process.

In an embodiment, and as an example, the effects of some AntiOxBENs on mitochondrial permeability transition pore (mPTP) opening were evaluated. In general, the tested AntiOxBENs had no effect per se on mPTP opening for all tested concentrations.

Figure 6A:
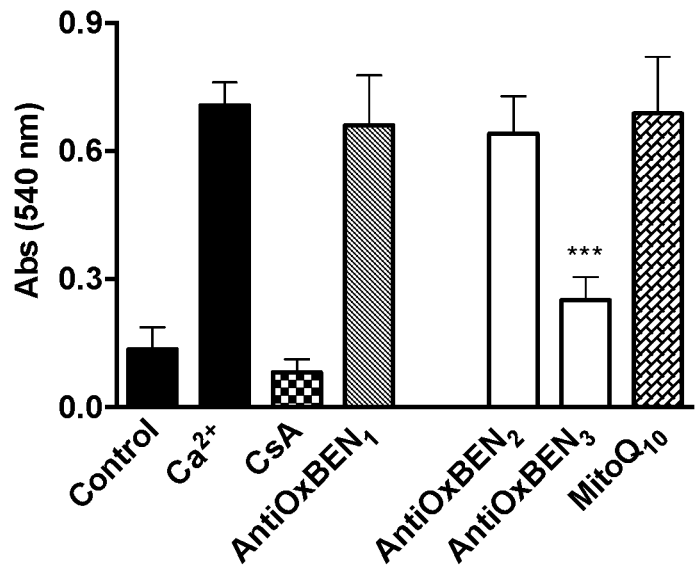
FIG. 6: Effect of AntiOxBENs and MitoQ on mitochondrial swelling upon induction of the mitochondrial permeability transition pore (mPTP). AntiOxBENs and MitoQ at (A) 2.5 µM, (B) 5 µM and (C) 10 µM were pre-incubated with RLM for 5 min before calcium addition. The comparisons were performed using one-way ANOVA between control ($Ca^{2+}$ only) vs. assays where AntiOxBEN derivatives were pre-incubated before $Ca^{2+}$. CsA-cyclosporin A.
Figure 6B:
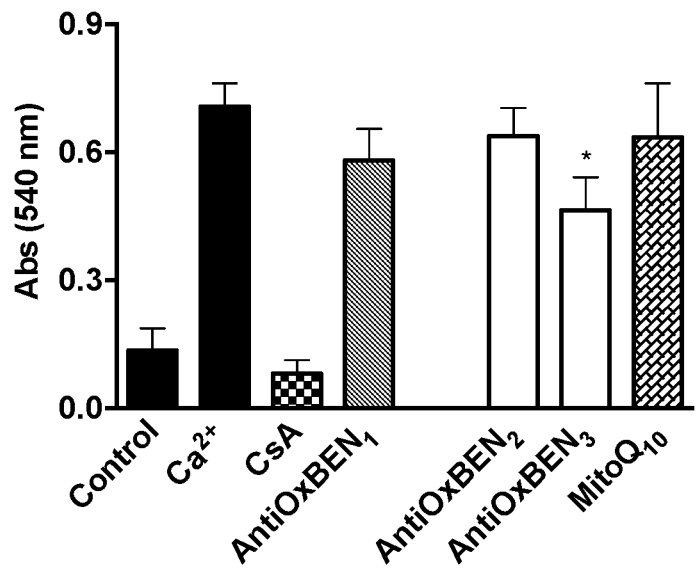
Figure 6C:
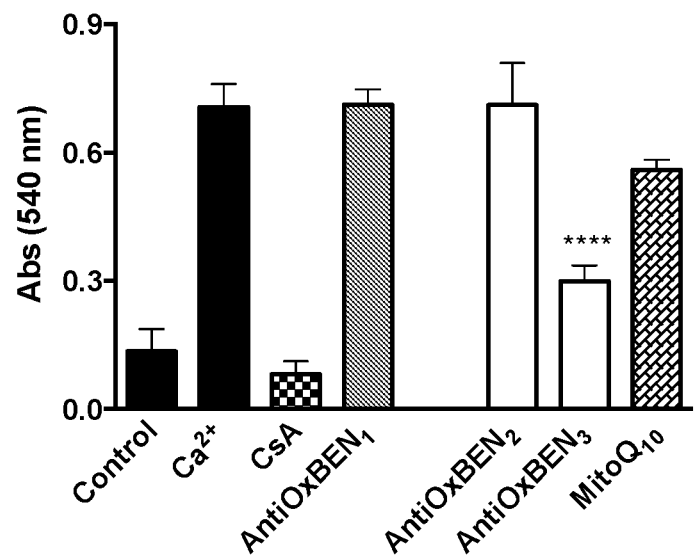

In an embodiment, it was found that AntiOxBEN$_3$, but not AntiOxBEN$_1$ and AntiOxBEN$_2$ and MitoQ, caused a concentration-dependent inhibition of calcium-dependent mPTP opening (FIG. 6A-C). This effect was comparable to that of cyclosporine A (1 μM), a classic mPTP desensitizer, and may be related with its antioxidant activity or by a possible chelation of calcium ions. This property can be of therapeutic interest, for instance to prevent and treat graft-versus host rejection in transplants, which normally involve mitochondrial disruption in the graft.

As cellular metabolism depends on optimal mitochondrial function the compounds' effects on mitochondria functional parameters can give information about their toxicity profile. So, their capacity to induce mitochondrial dysfunction by damaging the inner mitochondrial membrane or by inhibiting the respiratory chain, ATP synthesis, mitochondrial permeability transition pore (mPTP) process or export machinery was evaluated.

In an embodiment, and as an example, the toxicity effects of some AntiOxBENs and MitoQ on the mitochondrial bioenergetics, namely on RLM Δψ and respiration parameters, were measured. The Δψ represents the main component of the electrochemical gradient generated by mitochondrial respiration and accounts for more than 90% of the total available energy. For mitochondrial respiration assays, glutamate/malate (for complex I) and succinate (for complex II) were used as substrates. In addition, the mitochondrial oxidative phosphorylation coupling index, known as respiratory control ratio (RCR, state 3/state 4 respiration) and ADP/O index (the coupling between ATP synthesis and oxygen consumption) were also calculated. AntiOxBENs and MitoQ were tested at antioxidant-relevant concentrations, with 10 μM being the highest concentration.

In an embodiment, the mitochondrial bioenergetics data obtained for MitoQ was shown in Table 2. The results obtained have been used for comparative analysis.

TABLE 2

Effect of MitoQ on mitochondrial bioenergetics: mitochondrial respiratory control ratio (RCR), efficiency of the phosphorylative system (ADP/O), and mitochondrial transmembrane potential (ΔΨ).

| Mitochondrial | | | MitoQ | | |
|---|---|---|---|---|---|
| Bioenergetics | | Control | 2.5 μM | 5 μM | 10 μM |
| Glutamate/Malate | Maximum potential (ΔΨ in - mV) | 229.8 ± 17.4 | 195.7 ± 10.8 | 188.3 ± 10.6 | 113.8 ± 10.2 ** |
| | ADP-induced depolarization (ΔΨ in - mV) | 198.8 ± 13.3 | 173.0 ± 9.4 | 173.5 ± 8.9 | |
| | Repolarization Potential (ΔΨ in - mV) | 218.9 ± 13.7 | 191.1 ± 11.7 | 185.0 ± 9.4 | |
| | Lag Phase (s) | 105.3 ± 15.5 | 86.5 ± 5.6 | 84.5 ± 7.1 | |
| | RCR | 7.3 ± 0.6 | 4.2 ± 0.6 ** | 2.7 ± 0.3 **** | 1.3 ± 0.1 **** |
| | ADP/O | 2.6 ± 0.1 | 2.2 ± 0.1 * | 1.9 ± 0.1 **** | 2.0 ± 0.2 *** |
| Succinate | Maximum potential (ΔΨ in - mV) | 186.1 ± 6.6 | 181.6 ± 8.3 | 170.2 ± 8.1 | 108.9 ± 3.8 *** |
| | ADP-induced depolarization (ΔΨ in - mV) | 16.5 ± 6.5 | 162.1 ± 6.0 | 157.1 ± 6.4 | |
| | Repolarization Potential (ΔΨ in - mV) | 184.0 ± 6.4 | 182.7 ± 9.2 | 170.7 ± 8.7 | |
| | Lag Phase (s) | 123.4 ± 14.2 | 104.8 ± 9.9 | 92.6 ± 19.4 | |
| | RCR | 4.1 ± 0.3 | 2.6 ± 0.2 ** | 2.4 ± 0.2 *** | |
| | ADP/O | 1.5 ± 0.1 | 1.3 ± 0.1 * | 1.3 ± 0.1 * | |

*, , *, **** Statistically significant compared with control using Student's two tailed t-test.

Figure 7A:
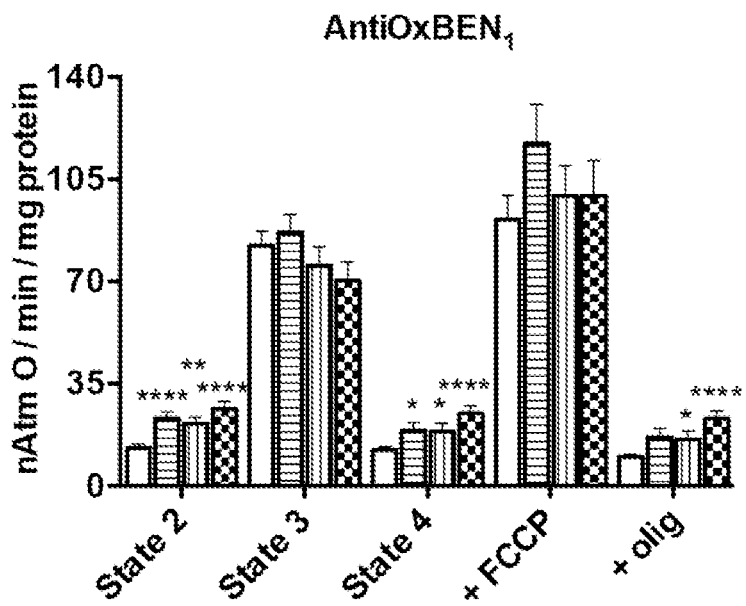
FIG. 7: Effect of AntiOxBENs and MitoQ on RLM respiration supported by (A) 10 mM glutamate+5 mM malate or (B) 5 mM succinate. White bars, control; Bars with horizontal pattern, 2.5 µM, Bars with vertical pattern, 5 µM, Bars with checkered pattern, 10 µM). The statistical significance relative to the different respiratory rates/states was determined using Student's two tailed t-test.
Figure 7A:
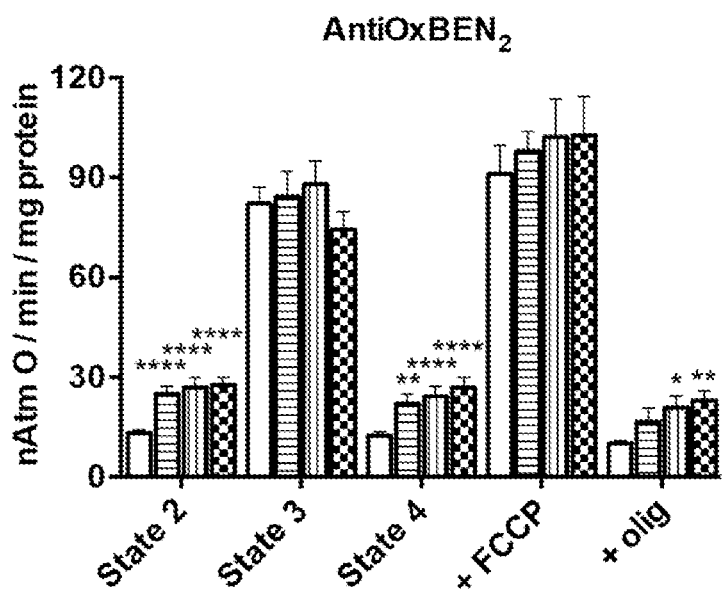
Figure 7B:
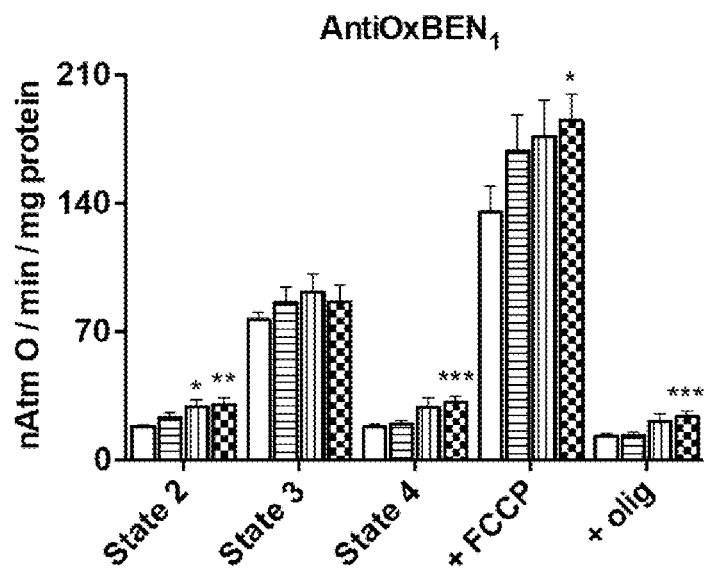
Figure 7B:
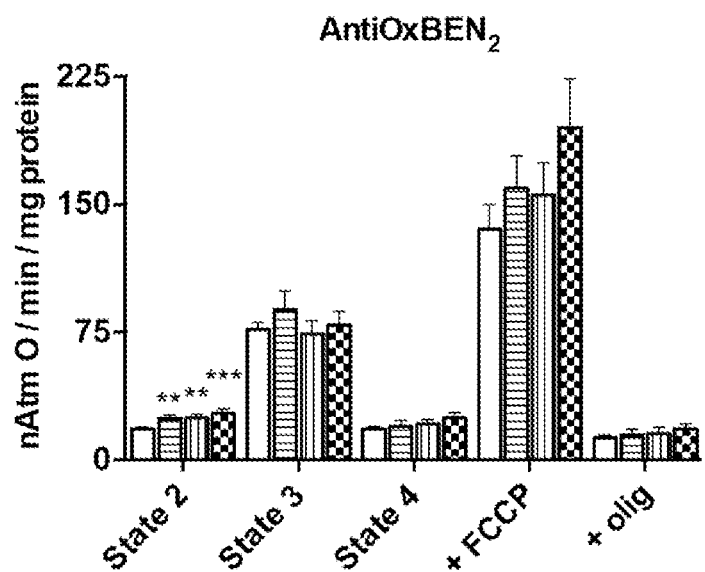

In an embodiment, it was observed that MitoQ, for all tested concentrations, caused a significant decrease of RCR and ADP/O parameters (Table 2). Moreover, when RLM were incubated with MitoQ concentrations up to 2.5 μM an increase on state 2, state 4 and oligomycin-inhibited respiration and a decrease on state 3 and FCCP-uncoupled respiration, using glutamate/malate as substrate was observed (FIG. 7A). When using succinate, RLM were completely uncoupled in the presence of MitoQ at the highest concentration tested (FIG. 7B). The incubation with increasing concentrations of MitoQ resulted in a progressive decrease of the maximum Δψ obtained upon energization (Table 2). Δψ collapse after ADP addition was observed with 10 μM MitoQ, since no repolarization occurred after ADP-induced depolarization (Table 2).

In an embodiment, and as an example, the highest concentration used in AntiOxBENs toxicity studies was the one in which MitoQ completely disrupted mitochondrial bioenergetics. The data of AntiOxBENs toxicity studies are shown in Tables 3 to 5.

In an embodiment, and as an example, AntiOxBENs, after glutamate/malate-energization, caused a slight ΔΨ dose-dependent depolarization (10-20 mV) while promoted a slight hyperpolarization of 5-20 mV under succinate-energization. Still, it is important to remark that AntiOxBENs do not significantly affect RLM ΔΨ.

TABLE 3

Effect of $AntiOxBEN_1$ on mitochondrial bioenergetics: mitochondrial respiratory control ratio (RCR), efficiency of the phosphorylative system (ADP/O), and mitochondrial transmembrane potential (ΔΨ).

| Mitochondrial Bioenergetics | | Control | $MitoBEN_1$ | | |
| --- | --- | --- | --- | --- | --- |
| | | | 2.5 μM | 5 μM | 10 μM |
| Glutamate/Malate | Maximum potential (ΔΨ in - mV) | 229.8 ± 17.4 | 216.8 ± 18.9 | 224.8 ± 24.7 | 200.4 ± 16.0 |
| | ADP-induced depolarization (ΔΨ in - mV) | 198.8 ± 13.3 | 199.5 ± 16.6 | 209.4 ± 20.3 | 192.6 ± 15.0 |
| | Repolarization Potential (ΔΨ in - mV) | 218.9 ± 13.7 | 212.3 ± 18.2 | 219.0 ± 22.9 | 199.4 ± 17.1 |
| | Lag Phase (s) | 105.3 ± 15.5 | 131.8 ± 18.9 | 137.8 ± 22.5 | 148.7 ± 48.4 |
| | RCR | 7.3 ± 0.6 | 4.9 ± 0.6 * | 4.4 ± 0.6 ** | 2.6 ± 0.1 **** |
| | ADP/O | 2.6 ± 0.1 | 2.5 ± 0.2 | 2.8 ± 0.4 | 2.1 ± 0.1 ** |
| Succinate | Maximum potential (ΔΨ in - mV) | 186.1 ± 6.6 | 191.4 ± 18.2 | 184.9 ± 13.1 | 188.9 ± 14.8 |
| | ADP-induced depolarization (ΔΨ in - mV) | 16.5 ± 6.5 | 180.3 ± 17.1 | 175.4 ± 12.9 | 182.4 ± 14.4 |
| | Repolarization Potential (ΔΨ in - mV) | 184.0 ± 6.4 | 190.3 ± 17.4 | 181.0 ± 13.5 | 188.8 ± 15.8 |
| | Lag Phase (s) | 123.4 ± 14.2 | 120.0 ± 32.1 | 93.6 ± 29.2 | 105.0 ± 28.1 |
| | RCR | 4.1 ± 0.3 | 4.7 ± 0.3 | 3.0 ± 0.3 * | 2.8 ± 0.3 ** |
| | ADP/O | 1.5 ± 0.1 | 1.7 ± 0.03 | 1.6 ± 0.1 | 1.5 ± 0.1 |

*, , ** Statistically significant compared with control using Student's two tailed t-test.

TABLE 4

Effect of $AntiOxBEN_2$ on mitochondrial bioenergetics: mitochondrial respiratory control ratio (RCR), efficiency of the phosphorylative system (ADP/O), and mitochondrial transmembrane potential (ΔΨ).

| Mitochondrial Bioenergetics | | Control | $MitoBEN_2$ | | |
| --- | --- | --- | --- | --- | --- |
| | | | 2.5 μM | 5 μM | 10 μM |
| Glutamate/Malate | Maximum potential (ΔΨ in - mV) | 229.8 ± 17.4 | 217.8 ± 18.8 | 212.2 ± 19.8 | 209.5 ± 19.1 |
| | ADP-induced depolarization (ΔΨ in - mV) | 198.8 ± 13.3 | 200.5 ± 17.5 | 194.9 ± 15.6 | 200.1 ± 18.2 |
| | Repolarization Potential (ΔΨ in - mV) | 218.9 ± 13.7 | 216.8 ± 17.9 | 209.0 ± 17.8 | 208.4 ± 18.6 |
| | Lag Phase (s) | 105.3 ± 15.5 | 124.7 ± 19.2 | 147.5 ± 31.2 | 146.2 ± 30.9 |
| | RCR | 7.3 ± 0.6 | 4.3 ± 0.6 ** | 3.9 ± 0.5 ** | 2.9 ± 0.3 **** |
| | ADP/O | 2.6 ± 0.1 | 2.3 ± 0.3 | 2.3 ± 0.2 | 2.1 ± 0.2 * |
| Succinate | Maximum potential (ΔΨ in - mV) | 186.1 ± 6.6 | 197.6 ± 18.2 | 204.6 ± 18.1 | 199.8 ± 16.0 |

TABLE 4-continued

Effect of AntiOxBEN$_2$ on mitochondrial bioenergetics: mitochondrial respiratory control ratio (RCR), efficiency of the phosphorylative system (ADP/O), and mitochondrial transmembrane potential ($\Delta\Psi$).

| Mitochondrial Bioenergetics | Control | MitoBEN$_2$ | | |
|---|---|---|---|---|
| | | 2.5 μM | 5 μM | 10 μM |
| ADP-induced depolarization ($\Delta\Psi$ in - mV) | 16.5 ± 6.5 | 184.5 ± 19.2 | 191.2 ± 17.8 | 190.9 ± 16.8 |
| Repolarization Potential ($\Delta\Psi$ in - mV) | 184.0 ± 6.4 | 193.6 ± 17.8 | 200.4 ± 17.0 | 198.6 ± 17.2 |
| Lag Phase (s) | 123.4 ± 14.2 | 115.4 ± 21.0 | 118.0 ± 26.4 | 124.8 ± 37.2 |
| RCR | 4.1 ± 0.3 | 5.2 ± 0.9 | 3.8 ± 0.4 | 3.5 ± 0.3 |
| ADP/O | 1.5 ± 0.1 | 1.7 ± 0.1 | 1.7 ± 0.1 | 1.6 ± 0.04 |

*, , ** Statistically significant compared with control using Student's two tailed t-test.

TABLE 5

Effect of AntiOxBEN$_3$ on mitochondrial bioenergetics: mitochondrial respiratory control ratio (RCR), efficiency of the phosphorylative system (ADP/O), and mitochondrial transmembrane potential ($\Delta\Psi$).

| | Mitochondrial Bioenergetics | Control | MitoBEN$_3$ | | |
|---|---|---|---|---|---|
| | | | 2.5 μM | 5 μM | 10 μM |
| Glutamate/Malate | Maximum potential ($\Delta\Psi$ in - mV) | 229.8 ± 17.4 | 221.1 ± 20.2 | 221.4 ± 22.6 | 227.5 ± 26.3 |
| | ADP-induced depolarization ($\Delta\Psi$ in - mV) | 198.8 ± 13.3 | 202.9 ± 18.7 | 204.5 ± 21.6 | 216.4 ± 25.3 |
| | Repolarization Potential ($\Delta\Psi$ in - mV) | 218.9 ± 13.7 | 217.0 ± 17.7 | 216.4 ± 21.3 | 222.9 ± 25.4 |
| | Lag Phase (s) | 105.3 ± 15.5 | 137.5 ± 20.3 | 154.5 ± 21.5 | 143.0 ± 21.7 |
| | RCR | 7.3 ± 0.6 | 3.9 ± 0.5 ** | 3.9 ± 0.6 ** | 3.07 ± 0.6 **** |
| | ADP/O | 2.6 ± 0.1 | 2.3 ± 0.2 | 2.3 ± 0.1 | 2.0 ± 0.2 * |
| Succinate | Maximum potential ($\Delta\Psi$ in - mV) | 186.1 ± 6.6 | 203.6 ± 16.6 | 205.3 ± 19.4 | 207.9 ± 19.3 |
| | ADP-induced depolarization ($\Delta\Psi$ in - mV) | 16.5 ± 6.5 | 188.0 ± 19.7 | 191.1 ± 20.0 | 198.2 ± 19.3 |
| | Repolarization Potential ($\Delta\Psi$ in - mV) | 184.0 ± 6.4 | 198.4 ± 18.4 | 199.1 ± 19.2 | 207.5 ± 19.4 |
| | Lag Phase (s) | 123.4 ± 14.2 | 132.6 ± 22.7 | 119.8 ± 32.2 | 114.4 ± 24.3 |
| | RCR | 4.1 ± 0.3 | 4.1 ± 0.5 | 4.3 ± 0.7 | 3.9 ± 0.4 |
| | ADP/O | 1.5 ± 0.1 | 1.6 ± 0.1 | 1.6 ± 0.1 | 1.7 ± 0.1 |

*, , ** Statistically significant compared with control using Student's two tailed t-test.

In an embodiment, and as example, the AntiOxBENs and MitoQ rates for state 2, state 3, state 4, oligomycin-inhibited respiration and mitochondrial respiration assays, and succinate (was used as substrate FCCP-stimulated respiration) are shown in FIGS. 7A and B.

In an embodiment, it was found that AntiOxBENs induced alterations on the respiratory chain in a dose-dependent manner. In general, AntiOxBENs increased state 2, state 4 and oligomycin-inhibited respiration at concentrations higher than 2.5 μM in a process that is mainly dependent on their lipophilicity and not relying on their aromatic pattern (catechol vs pyrogallol). However, it must be stressed that the observed effects were more apparent by using complex I substrates. (FIGS. 7A and B).

In an embodiment, and as an example, it was shown that AntiOxBENs induced dose-dependent alterations in the respiratory profile of isolated RLM. Some of the observed effects can probably result from a membrane permeabilization effect or a proton shuttling activity. This effect may lead to stimulation of non-phosphorylation respiration and to a small $\Delta\psi$ depolarization. Consequently, AntiOxBENs, for all tested concentrations, caused a significant decrease of RCR. Moreover, AntiOxBENs (10 μM) also affected the mitochondrial phosphorylative system, as assessed by alterations in the ADP/O ratio.

In an embodiment, and as an example, AntiOxBENs mitochondrial toxicity observed at higher concentrations may be associated with the lipophilicity of the spacer and/or the presence of a TPP moiety and has little, if any, relation with their (catechol vs pyrogallol). Still, the presence of the TPP cation and a lipophilic spacer is essential for an efficient and sometimes extensive mitochondrial accumulation.

In an embodiment, and as an example, it was found that at higher concentrations, mitochondria-targeted antioxidants, AntiOxBENs and MitoQ, can disrupt mitochondrial respiration by causing damage in the inner mitochondrial membrane or by inhibiting the respiratory chain, ATP synthesis or export machinery.

In an embodiment, it must be stressed that MitoQ effectively inhibited lipid peroxidation in RLM at 5 μM (FIGS. 4 and 5) but caused toxicity on the mitochondrial bioenergetic apparatus of RLM at 2.5 μM (FIGS. 7A and B and Table 2).

In an embodiment, it was concluded that for the AntiOxBENs under study, RLM toxicity was detected at higher concentrations than the ones needed to exert antioxidant effect, independently of their mechanism.

In an embodiment, and as an example, it was concluded that in general AntiOxBENs showed a better safety profile than MitoQ.

Figure 8:
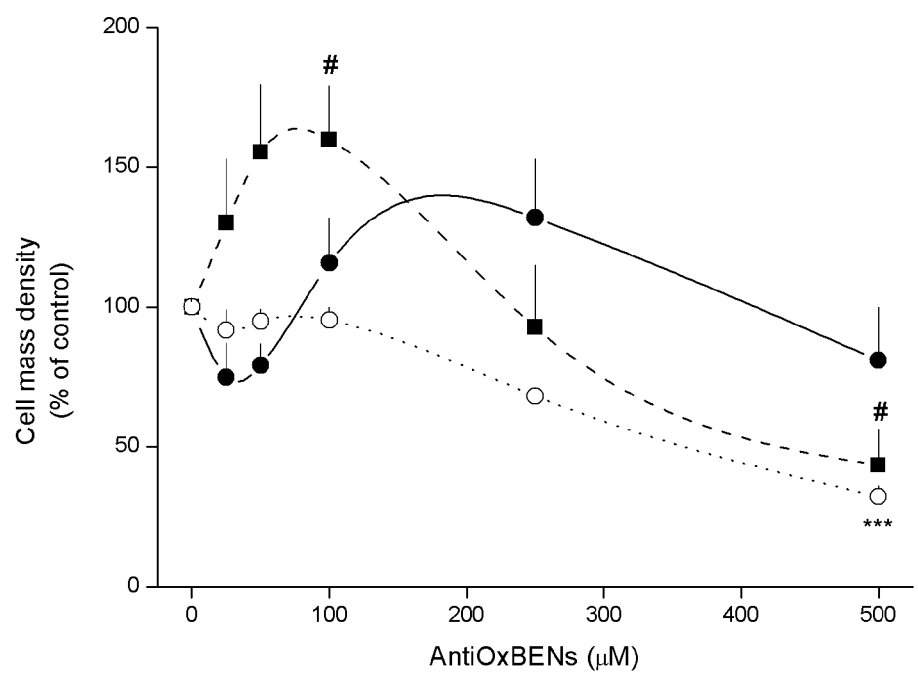
FIG. 8: Cytotoxicity profile of AntiOxBEN$_1$ (□), AntiOxBEN$_2$ (○) and AntiOxBEN$_3$ (⊙) on human hepatocellular carcinoma cells (HepG2) proliferation. Statistically significant compared with control group using one-way ANOVA.

In an embodiment, and as an example, the cytotoxicity of AntiOxBENs was assessed using monolayer cultures of human hepatocytes from hepatocellular carcinoma (HepG2) and SRB method (FIG. 8). From the data, it was concluded that AntiOxBENs exhibited low toxicity toward HepG2 cells (FIG. 8). Although AntiOxBEN$_1$ promote a small inhibition of cell proliferation for lower concentrations, at concentrations higher than 100 μM stimulated cell proliferation. Remarkably, at concentrations lower than 250 μM, AntiOxBEN$_2$ significantly stimulated cell proliferation, while at concentrations higher than 250 μM, significantly inhibited cell proliferation. AntiOxBEN$_3$, at concentrations higher than 250 μM, significantly inhibited cell proliferation.

In an embodiment, and as an example, it was concluded that AntiOxBENs toxicity, based on its properties (Table 1) and RLM accumulation rates (FIG. 3), can be mediated by compounds' lipophilicity. In general, AntiOxBENs have a safety margin towards HepG2 cells.

In an embodiment, and as an example, it was concluded that the structural modifications of benzoic acids (protocatechuic and gallic acids) led to a significant improvement of their mitochondriotropic properties. AntiOxBENs have increased antioxidant activity, higher mitochondrial accumulation and lower toxicity.

In an embodiment, the overall results showed that AntiOxBENs are accumulated inside mitochondria driven by the organelle transmembrane electric potential and prevented lipid peroxidation, exhibiting low intrinsic toxicity. AntiOxBENs present a higher lipophilicity than their parent compounds, for instance protocatechuic acid and gallic acid, and similar antioxidant and iron chelating properties.

In an embodiment, AntiOxBENs are mitochondriotropic antioxidants which are aimed to prevent or slow mitochondrial oxidative stress associated to aging and several pathologies, for instance diabetes, non-alcoholic fatty liver disease, cardiovascular diseases, acute pancreatitis and neurodegenerative diseases, including Alzheimer or Parkinson disease, and amyotrophic lateral sclerosis.

In an embodiment, and from AntiOxBENs series used as an example, the pyrogallol-based analogues are predicted to be potential candidates for development of a first class drugs with therapeutic application in mitochondrial oxidative-related disorders.

Examples of synthetic procedures followed to obtain and a number of intermediates and AntiOxBENs are provided.

In an embodiment, the structural characterization of the compounds was attained by spectrometric methods of analysis. $^1$H and $^{13}$C spectra NMR spectra were acquired at room temperature and recorded on a Bruker Avance III operating at 400 and 100 MHz, respectively. Chemical shifts are expressed in δ (ppm) values relative to tetramethylsilane (TMS) as internal reference and coupling constants (J) are given in Hz. Assignments were also made from DEPT (distortionless enhancement by polarization transfer) (underlined values). Mass spectra (MS) were recorded on a Bruker Microtof (ESI) or Varian 320-MS (EI) apparatus and referred in m/z (% relative) of important fragments.

In an embodiment, the reaction progress was assessed by thin layer chromatography (TLC) analyses on aluminium silica gel sheets 60 F254 plates (Merck, Darmstadt, Germany) in dichloromethane, ethyl acetate and dichloromethane/methanol, in several proportions. The spots were detected using UV detection (254 and 366 nm). Flash column chromatography was performed using silica gel 60 (0.040-0.063 mm) (Carlo Erba Reactifs—SDS, France).

In an embodiment, AntiOxBEN1 and AntiOxBEN2 obtention was performed following a four step synthetic strategy depicted in FIG. 1A. Firstly, the intermediate compounds 3 and 4 were synthesized as follows: 3,4-dimethoxybenzoic acid (1), or 3,4,5-trimethoxybenzoic acid (2), in particular 1 mmol, was dissolved in dichloromethane, in particular in 40 mL of dichloromethane and triethylamine, in particular in 2 mmol of triethylamine was added. Ethylchloroformate, in particular 2 mmol of ethylchloroformate was added dropwise to the stirred solution, kept in an ice bath. After stirring, in particular for 2 h at room temperature, the mixture was cooled again and 6-aminohexan-1-ol, in particular 2 mmol of 6-aminohexan-1-ol was added. The reaction was stirred, in particular during 10 h at room temperature. The mixture was extracted with dichloromethane, in particular 3 ⊠ 20 mL. The organic phases were combined, washed with water, NaHCO$_3$ 5%, in particular 20 mL of NaHCO$_3$ 5% and HCl 1 M, in particular 20 mL of HCl 1M. The organic phases were combined, dried and, after filtration, the solvent was evaporated to obtain a white residue. The reaction was followed by TLC, in particular silica gel, ethyl acetate.

In an embodiment, the characterization of N-(6-hydroxyhexyl)-3,4-dimethoxybenzamide (3) is as follows: yield of 74%; $^1$H NMR (400 MHz, CDCl$_3$): δ=1.39-1.41 (4H, M, (CH$_2$)$_2$(CH$_2$)$_2$OH), 1.55-1.63 (4H, M, NCH$_2$CH$_2$(CH$_2$)$_2$CH$_2$), 1.99 (1H, S, OH), 3.40-3.45 (2H, m, NCH$_2$), 3.63 (2H, t, J=6.5 Hz, CH$_2$OH), 3.91 (6H, s, 2×OCH$_3$), 6.38 (1H, t, J=5.2 Hz, CONH), 6.85 (1H, d, J=8.4 Hz, H(5)), 7.29 (1H, dd, J=8.4 Hz, J=2.0 Hz, H(6)), 7.43 (1H, d, J=2.0 Hz, H(2)). $^{13}$C NMR (100 MHz, CDCl$_3$): δ=25.4 (CH$_2$(CH$_2$)$_2$OH), 26.7 (N(CH$_2$)$_2$CH$_2$), 29.8 (NCH$_2$CH$_2$), 32.6 (CH$_2$CH$_2$OH), 40.0 (NCH$_2$), 56.1 (2×OCH$_3$), 62.7 (CH$_2$OH), 110.4 (C(5)), 110.7 (C(2)), 119.4 (C(6)), 127.5 (C(1)), 149.0 (C(3)), 151.7 (C(4)), 167.3 (CONH). EI-MS m/z (%): 281 (M.+), 208 (16), 195 (21), 194 (100), 180 (16), 165 (75), 164 (55), 121 (15).

In an embodiment, the characterization of N-(6-hydroxyhexyl)-3,4,5-trimethoxybenzamide (4) is as follows: yield of 82%; $^1$H NMR (400 MHz, CDCl$_3$): δ=1.40-1.43 (4H, m, (CH$_2$)$_2$(CH$_2$)$_2$OH), 1.54-1.66 (4H, m, NCH$_2$CH$_2$(CH$_2$)$_2$CH$_2$), 1.81 (1H, s, OH), 3.41-3.46 (2H, m, NCH$_2$), 3.64 (2H, t, J=6.4 Hz, CH$_2$OH), 3.87 (3H, s, OCH$_3$), 3.89 (6H, s, 2×OCH$_3$), 6.28 (1H, t, J=5.1 Hz, CONH), 7.00 (2H, s, H(2) and H(6)); $^{13}$C NMR (100 MHz, CDCl$_3$): δ=25.4 (CH$_2$(CH$_2$)$_2$OH), 26.7 (NCH$_2$CH$_2$CH$_2$), 29.8 (NCH$_2$CH$_2$), 32.6 (CH$_2$CH$_2$OH), 40.1 (NCH$_2$), 56.4 (2× OCH$_3$), 61.0 (OCH$_3$), 62.8 (CH$_2$OH), 104.5 (C(2) and C(6)), 130.4 (C(1)), 140.9 (C(4)), 153.3 (C(3) and C(5)), 167.5 (CONH) and EI-MS m/z (%): 312 (M.+), 225 (38), 224 (34), 211 (59), 196 (49), 195 (100).

In an embodiment, the general synthetic procedure for obtention of bromohexylbenzamides compounds 5 and 6 is as follows: N-(6-hydroxyhexyl)-3,4-dimethoxybenzamide (3), or N-(6-hydroxyhexyl)-3,4,5-trimethoxybenzamide (4), in particular 1 mmol of hydroxyhexylbenzamide 3, or hydroxyhexylbenzamide 4, and 1,2-dibromotetrachloroethane, in particular 1 mmol of 1,2-dibromotetrachloroethane was dissolved in THF, in particular in 20 mL of THF. After adding 1,2-bis(diphenylphosphine)ethane (diphos), in particular 0.5 mmol, the reaction was stirred, in particular at room temperature for 20 hours. Then, the reaction mixture was filtered, in particular through a Celite pad. After evaporation of the filtrate an oil residue was obtained. The oil was purified, in particular by silica gel flash chromatography using ethyl acetate as eluting system. The fractions containing the intended compound were collected, the solvent evaporated and the products were recrystallized from n-hexane. The reaction was followed by TLC, in particular silica gel, ethyl acetate.

In an embodiment, the N-(6-bromohexyl)-3,4-dimethoxybenzamide (5) is characterized as follows: yield of 66%; $^1$H NMR (400 MHz, CDCl$_3$): δ=1.38-1.53 (4H, m, (CH$_2$)$_2$(CH$_2$)$_2$Br), 1.59-1.67 (2H, m, NCH$_2$CH$_2$), 1.83-1.90 (2H, m, CH$_2$CH$_2$Br), 3.39-3.46 (4H, m, NCH$_2$(CH$_2$)$_4$CH$_2$Br), 3.92 (6H, s, 2×OCH$_3$), 6.25 (1H, t, J=5.4 Hz, CONH), 6.85 (1H, d, J=8.4 Hz, H(5)), 7.27 (1H, dd, J=8.4 Hz, J=2.0 Hz, H(6)), 7.43 (1H, d, J=2.0 Hz, H(2)); $^{13}$C NMR (100 MHz, CDCl$_3$): δ=26.2 (NCH$_2$CH$_2$CH$_2$), 28.0 (CH$_2$(CH$_2$)$_2$Br), 29.7 (NCH$_2$CH$_2$), 32.7 (CH$_2$CH$_2$Br), 33.9 (CH$_2$Br), 40.0 (NCH$_2$), 56.1 (OCH$_3$×2), 110.3 (C(5)), 110.7 (C(2)), 119.2 (C(6)), 127.5 (C(1)), 149.1 (C(3)), 151.7 (C(4)), 167.2 (CONH) and EI-MS m/z (%): 345 (M.+), 343 (24), 264 (36), 195 (34), 194 (19), 181 (40), 166 (24), 165 (100).

In an embodiment, the N-(6-bromohexyl)-3,4,5-trimethoxybenzamide (6) is characterized as follows: yield of 75%; $^1$H NMR (400 MHz, CDCl$_3$): δ=1.37-1.52 (4H, m, (CH$_2$)$_2$(CH$_2$)$_2$Br), 1.59-1.66 (2H, m, NCH$_2$CH$_2$), 1.83-1.90 (2H, m, CH$_2$CH$_2$Br), 3.39-3.45 (4H, m, NCH$_2$(CH$_2$)$_4$CH$_2$Br), 3.87 (3H, s, OCH$_3$), 3.88 (6H, s, 2×OCH$_3$), 6.40 (1H, t, J=5.3 Hz, CONH), 7.01 (2H, s, H(2) and H(6)); $^{13}$C NMR (100 MHz, CDCl$_3$): δ=26.2 (NCH$_2$CH$_2$CH$_2$), 27.9 (CH$_2$(CH$_2$)$_2$Br), 29.6 (NCH$_2$CH$_2$), 32.6 (CH$_2$CH$_2$Br), 33.9 (CH$_2$Br), 40.1 (NCH$_2$), 56.4 (2×OCH$_3$), 61.0 (OCH$_3$), 104.4 (C(2) and C(6)), 130.3 (C(1)), 140.8 (C(4)), 153.2 (C(3) and C(5)), 167.3 (CONH) and EM/EI m/z (%): 374 (M.+), 372 (15), 225 (18), 224 (100), 210 (18), 195 (32), 194 (48).

In an embodiment, the bromohexylbenzamide 5, or 6, (1 mmol) was mixed with triphenylphosphine (PPh3) (1 mmol) in a round-bottomed flask and heated to a temperature of approximately 120° C. for 48 hours. The residue was purified by silica gel flash chromatography using gradient elution (ethyl acetate:methanol). The fractions containing the desired compound were collected and the solvent was evaporated to dryness. The reaction was followed by TLC (silica gel, ethyl acetate:methanol (9:1) and dichloromethane:methanol (9:1)).

In an embodiment, the 6-(3,4-dimethoxybenzamido)hexyltriphenylphosphonium bromide (7) is characterized as follows: yield of 65%; $^1$H NMR (400 MHz, CD$_3$OD): δ=1.40-1.72 (8H, m, NCH$_2$(CH$_2$)$_4$), 3.33-3.37 (2H, m, CH$_2$P+Ph$_3$), 3.42-3.49 (2H, m, NCH$_2$), 3.83 (6H, s, 2×OCH$_3$), 6.98 (1H, d, J=8.5 Hz, H(5)), 7.46 (1H, d, J=2.1 Hz, H(2)), 7.49 (1H, dd, J=8.5, J=2.1 Hz, Hz, H(6)), 7.73-7.89 (15H, m, PPh$_3$); $^{13}$C NMR (100 MHz, CD$_3$OD): δ=22.7 (d, J$_{CP}$=51.0 Hz, CH$_2$P+Ph$_3$), 23.5 (d, J$_{CP}$=4.3 Hz, CH$_2$(CH$_2$)$_2$P+Ph$_3$), 27.2 (CH$_2$(CH$_2$)$_3$P+Ph$_3$), 30.3 (NCH$_2$CH$_2$), 31.2 (d, J$_{CP}$=16.3 Hz, CH$_2$CH$_2$P+Ph$_3$), 40.8 (NCH$_2$), 56.7 (2×OCH$_3$), 112.0 (C(5)), 112.2 (C(2)), 120.0 (d, J$_{CP}$=86.2 Hz, C(1')), 122.0 (C(6)), 128.1 (C(1)), 131.6 (d, J$_{CP}$=12.6 Hz, C(3') and C(5')), 134.9 (d, J$_{CP}$=10.0 Hz, C(2') and C(6')), 136.3 (d, J$_{CP}$=3.0 Hz, C(4')), 150.2 (C(3)), 153.4 (C(4)), 169.5 (CONH) and EI-MS m/z (%): 511 (M.+), 277 (37), 263 (40), 262 (100), 183 (87), 165 (47), 151 (35), 108 (44), 107 (29), 77 (26), 52 (26).

In an embodiment, the 6-(3,4,5-trimethoxybenzamido)hexyltriphenylphosphonium bromide (8) is characterized as follows: yield of 79%; $^1$H NMR (400 MHz, CD$_3$OD): δ=1.41-1.73 (8H, m, NCH$_2$(CH$_2$)$_4$), 3.37-3.40 (2H, m, CH$_2$P+Ph$_3$), 3.50-3.56 (2H, m, NCH$_2$), 3.94 (3H, s, OCH$_3$), 3.95 (9H, s, 2×OCH$_3$), 7.28 (2H, s, H(2) and H(6)), 7.75-7.90 (15H, m, PPh$_3$); $^{13}$C NMR (100 MHz, CD$_3$OD): δ=22.5 (d, J$_{CP}$=50.8 Hz, CH$_2$P+Ph$_3$), 23.3 (d, J$_{CP}$=4.0 Hz, CH$_2$(CH$_2$)$_2$P+Ph$_3$), 27.1 (CH$_2$(CH$_2$)$_3$P+Ph$_3$), 30.0 (NCH$_2$CH$_2$), 30.9 (d, J$_{CP}$=16.2 Hz, CH$_2$CH$_2$P+Ph$_3$), 40.6 (NCH$_2$), 57.0 (2×OCH$_3$), 61.1 (OCH$_3$), 106.0 (C(2) and C(6)), 119.7 (d, J$_{CP}$=86.1 Hz, C(11), 130.8 (C(1)), 131.4 (d, J$_{CP}$=12.5 Hz, C(3') and C(5')), 134.7 (d, J$_{CP}$=10.0 Hz, C(2') and C(6')), 136.1 (d, J$_{CP}$=2.8 Hz, C(4')), 141.6 (C(4)), 154.1 (C(3) and C(5)), 168.7 (CONH) and EI-MS m/z (%): 448 (M.+), 446 (41), 278 (35), 277 (81), 276 (27), 275 (58), 263 (29), 262 (100), 185 (31), 184 (25), 183 (94), 152 (21), 108 (36), 96 (53), 94 (54), 77 (24), 58 (41).

In an embodiment, the triphenylphosphonium salt 7, or 8, in particular 1 mmol of triphenylphosphonium salt 7, or 1 mmol of triphenylphosphonium salt 8, was dissolved in anhydrous dichloromethane, in particular in 15 mL of anhydrous dichloromethane. The reaction mixture was stirred under argon and cooled at a temperature below −70° C. Boron tribromide, in particular 5-7 mmol of boron tribromide, 1 M solution in dichloromethane, was added to the solution and the reaction was kept, in particular at −70° C. for 10 minutes. After reach room temperature, the reaction was continued for 12 hours. Thereafter, the reaction was finished by cautious addition of water, in particular 40 mL of water. After removing water, the resulting product was dissolved in methanol and dried, filtered and the solvent evaporated. The residue was purified, in particular by silica gel flash chromatography using gradient elution, in particular dichloromethane:methanol. The fractions containing the desired compound were collected and the solvent was evaporated to dryness. The reaction was followed by TLC, in particular silica gel, dichloromethane:methanol (9:1). The resulting residue was crystallized from ethyl ether/methanol to give the corresponding triphenylphosphonium bromide salt.

In an embodiment, the structural characterization of the 6-(3,4-dihydroxybenzamido)hexyltriphenylphosphonium bromide (AntiOxBEN$_1$) was follows: yield of 60%; $^1$H NMR (400 MHz, CD$_3$OD): δ=1.35-1.47 (2H, m, N(CH$_2$)$_4$CH$_2$), 1.50-1.75 (6H, m, NCH$_2$(CH$_2$)$_3$), 3.33-3.47 (4H, m, NCH$_2$(CH$_2$)$_4$CH$_2$P+Ph3), 6.79 (1H, d, J=8.3 Hz, H(5)), 7.18 (1H, dd, J=8.3 Hz, J=2.2 Hz, H(6)), 7.26 (1H, d, J=2.2 Hz, H(2)), 7.69-7.92 (15H, m, PPh$_3$); $^{13}$C NMR (100 MHz, CD$_3$OD): δ=22.7 (d, J$_{CP}$=51.2 Hz, CH$_2$P+Ph$_3$), 23.4 (d, J$_{CP}$=4.5 Hz, CH$_2$(CH$_2$)$_2$P+Ph$_3$), 27.0 (CH$_2$(CH$_2$)$_3$P+Ph$_3$), 30.1 (NCH$_2$CH$_2$), 31.0 (d, J$_{CP}$=16.2 Hz, CH$_2$CH$_2$P+Ph$_3$), 40.0 (NCH$_2$), 115.7 (C(5)), 115.8 (C(2)), 120.0 (d, J$_{CP}$=86.4 Hz, C(1')), 120.5 (C(6)), 126.9 (C(1)), 131.5 (d, J$_{CP}$=12.5 Hz, C(3') and C(5')), 134.8 (d, J$_{CP}$=9.9 Hz, C(2') and C(6')), 136.3 (d, J$_{CP}$=3.0 Hz, C(4')), 146.3 (C(3)), 150.1 (C(4)), 170.3 (CONH) and ME/ESI m/z (%): 499 (M++H—Br, 51), 498 (M+—Br, 98), 399 (31), 397 (31), 291 (100), 277 (67).

In an embodiment, the structural characterization of the 6-(3,4,5-trihydroxybenzamido)hexyltriphenylphosphonium bromide (AntiOxBEN$_2$) is as follows: yield of 50%; $^1$H NMR (400 MHz, DMSO): δ=1.23-1.50 (8H, m, NCH$_2$(CH$_2$)

₄), 3.11-3.16 (2H, m, CH₂P⁺Ph3), 3.54-3.59 (2H, m, NCH₂), 6.81 (2H, s, H(2) and H(6)), 7.74-7.91 (15H, m, PPh₃), 8.00 (1H, t, J=5.1 Hz, CONH); ¹³C NMR (100 MHz, DMSO): δ= 20.2 (d, J$_{CP}$=49.8 Hz, CH₂P⁺Ph₃), 21.8 (d, J$_{CP}$=4.1 Hz, CH₂(CH₂)₂P⁺Ph₃), 25.6 (CH₂(CH₂)₃P⁺Ph₃), 28.9 (NCH₂ CH₂), 29.6 (d, J$_{CP}$=16.6 Hz, CH₂CH₂P⁺Ph₃), 38.9 (NCH₂), 106.7 (C(2) and C(6)), 118.6 (d, J$_{CP}$=85.6 Hz, C(1')), 125.1 (C(1)), 130.3 (d, J$_{CP}$=12.4 Hz, C(3') and C(5')), 133.6 (d, J$_{CP}$=10.1 Hz, C(2') and C(6')), 134.9 (d, J$_{CP}$=2.7 Hz, C(4')), 136.1 (C(4)), 145.4 (C(3) and C(5)), 166.3 (CONH) and ME/ESI m/z (%): 526 (M++Na—Br, 62), 515 (M++H—Br, 30), 514 (M+—Br, 100), 277 (24).

Figure 1B:
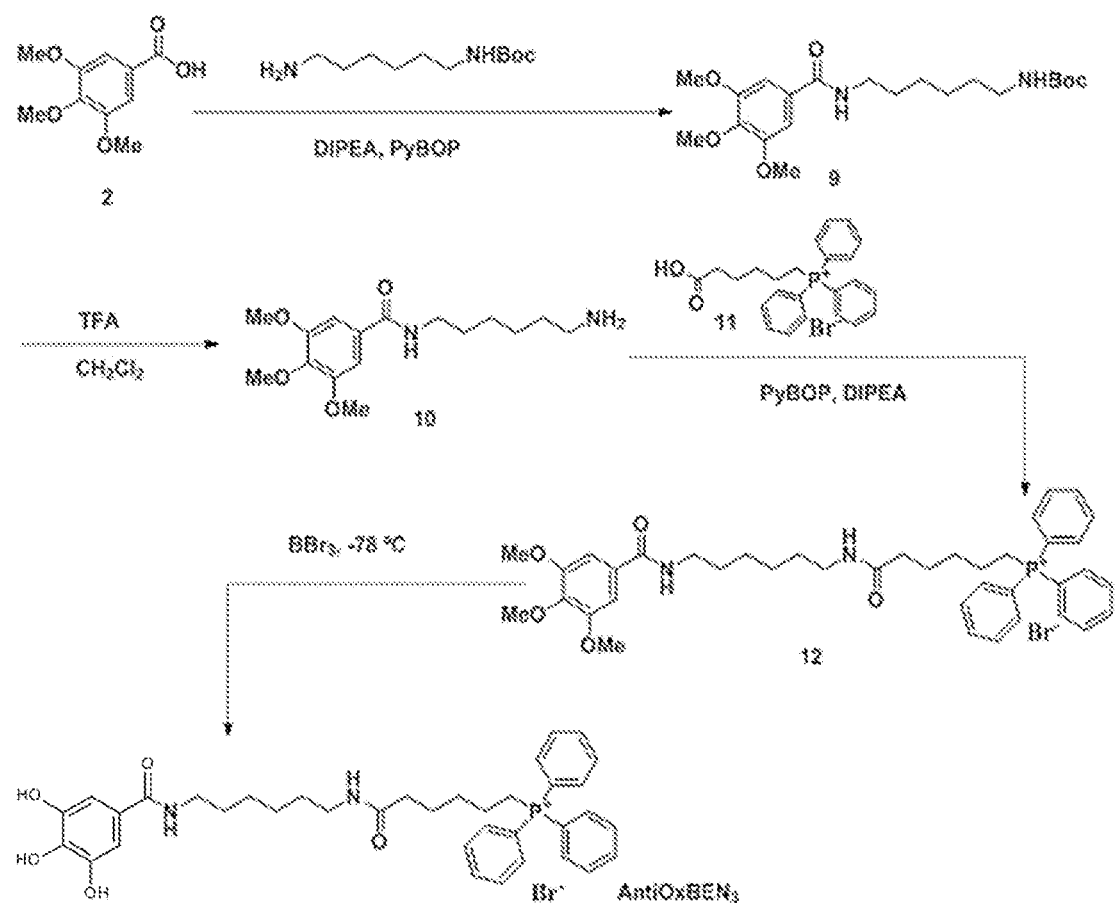

In an embodiment, AntiOxBEN₃ was performed following a four step synthetic strategy depicted in FIG. 1B. Firstly, the 3,4,5-trimethoxybenzoic acid (2), (500 mg, 2.3 mmol) was dissolved in DMF (3.9 mL) at 4° C. and then N,N-diethylpropan-2-amine (0.421 ml, 2.3 mmol) and PyBOP (1668 mg, 2.3 mmol) in CH₂Cl₂ (3.9 mL) were added. The mixture was kept in an ice bath and stirred for half hour. After this period tert-butyl (6-aminohexyl)carbamate (0.529 ml, 2.3 mmol) was added and the mixture was allowed to warm up to room temperature. The reaction was kept with stirring during 18 hours. Then the mixture was diluted with dichloromethane (20 mL) and washed with saturated NaHCO₃ solution (2×10 mL). The organic phase was dried over Na₂SO₄, filtered and concentrated under reduced pressure. The residue was purified by flash chromatography (50% AcOEt/Petroleum ether) and a yield of 73% was obtained.

In an embodiment, the structural characterization of the compound tert-butyl (6-(3,4,5-trimethoxybenzamido)hexyl) carbamate) (9) was as follows: ¹H NMR (400 MHz, CDCl₃): δ=7.07 (2H, s, H5, H6), 6.55 (1H, s, H1'), 4.59 (1H, s, H8'), 3.91 (6H, s, 2×OCH₃), 3.88 (3H, s, OCH₃), 3.43 (2H, dd, J=13.0, 6.9 Hz, H2'), 3.13 (1H, dd, J=12.6, 6.2 Hz, H7'), 1.67-1.58 (2H, m, H3'), 1.53-1.32 (15H, m, H4', H5', H6', NHCOOC(CH₃)); and ¹³C NMR (100 MHz, CDCl₃): δ=167.3 (CON H), 156.3 (NHCOOC(CH₃)), 153.3 (C3, C5), 140.9 (C4), 130.4 (C1), 104.5 (C2, C6), 79.3 (NHCOO C(CH₃)), 61.0 (OCH₃), 56.4 (2×OCH₃), 40.0 (C7'), 39.7 (C1'), 30.2 (C2'), 29.5 (C6'), 28.5 (NHCOOC(CH₃)), 26.1 (C3'), 25.8 (C4').

In an embodiment, the synthesis of N-(6-aminohexyl)-3,4,5-trimethoxybenzamide (10) was as follows: the deprotection step was performed adding TFA (4 ml) to a solution of 9 (1 g, 2.4 mmol) in CH₂Cl₂ (8 ml). The reaction was stirred at room temperature for one hour. After neutralization with a saturated NaHCO₃ solution, the organic phase was separated. The organic phase was dried over Na₂SO₄, filtered and concentrated under reduced pressure. The residue was purified by flash chromatography (10% MeOH/CH₂Cl₂) with a yield of 98%.

In an embodiment, the structural characterization of the compound N-(6-aminohexyl)-3,4,5-trimethoxybenzamide (10) was as follows: ¹H NMR (400 MHz, MeOD): δ=7.19 (2H, s, H2, H6), 3.89 (6H, s, 2×OCH₃), 3.80 (3H, s, OCH₃), 3.39 (1H, t, J=7.1 Hz, H2), 2.99-2.90 (2H, m, H7), 1.77-1.55 (4H, m, H3, H6), 1.50-1.36 (4H, m, H4, H5); and ¹³C NMR (100 MHz, MeOD): δ=169.4 (CONH), 154.3 (C3, C5), 141.8 (C4'), 131.1 (C1), 105.9 (C2, C6), 61.2 (OCH₃), 56.7 (2×OCH₃), 40.8 (C7'), 40.6 (C1'), 30.2 (C6', 28.4 (C3'), 27.4 (C4'), 27.0 (C5').

In an embodiment, the synthesis of [5-(6-(3,4,5-trimethoxybenzamido)hexylamino)carbonylpentyl] triphenylphosphonium bromide (12) was as follows: to a solution of 10 (689 mg, 2.2 mmol) in DMF (7.4 mL) at 4° C. N,N-diethylpropan-2-amine (0.476 ml, 2.7 mmol) and PyBOP (1572 mg, 2.7 mmol) in CH₂Cl₂ (7.4 mL) were added. The mixture was kept in an ice bath and stirred for half hour. After this period, compound 11 (1218, 2.7 mmol) was added and then the reaction was heated up to room temperature. The reaction was kept under stirring for 20 hours. Then the mixture was diluted with AcOEt (40 mL) and washed with saturated NaHCO₃ solution (2×10 mL). The organic phase was dried over Na₂SO₄, filtered and concentrated under reduced pressure. The residue was purified by flash chromatography (10% MeOH/CH₂C₁₂), yield: 63%.

In an embodiment, the structural characterization of the compound [5-(6-(3,4,5-trimethoxybenzamido)hexylamino) carbonylpentyl] triphenylphosphonium bromide (12) was as follows: ¹H NMR (400 MHz, CDCl₃): δ=7.85-7.76 (3H, m, H4''), 7.73-7.59 (12H, m, H2'', H3'', H5'', H6''), 7.12 (2H, s, H2, H6), 6.93 (1H, t, J=5.7 Hz, H1'), 6.26 (1H, t, J=5.7 Hz, H8'), 3.88 (6H, s, 2×OCH₃), 3.85 (1H, s, OCH₃), 3.39 (dd, J=13.2, 6.7 Hz, 1H), 3.19-3.05 (4H, m, H7', H14'), 2.14 (1H, t, J=7.1 Hz, H10'), 1.69-1.26 (14H, m, H3', H4', H5', H6' H11', H12', H13'); and ¹³C NMR (100 MHz, CDCl₃): δ=173.3 (C9'), 167.2 (PhCONH), 153.1 (C3, C5), 140.4 (C4), 135.4 (d, J$_{CP}$=2.9 Hz, C4''), 133.4 (d, J$_{CP}$=9.9 Hz, C2'',C6''), 130.7 (d, J$_{CP}$=12.6 Hz, C3'',C5''), 130.4 (C1), 117.9 (d, J$_{CP}$=86.2 Hz, C1''), 104.5 (C2, C6), 60.9 (OCH₃), 56.4 (2×OCH₃), 39.7 (C2'), 39.0 (C7'), 36.3 (C10'), 30.0 (C3'), 29.8 (C6'), 28.9 (d, J=5.0 Hz, C12'), 26.6 (C4'), 25.9 (C5'), 24.9 (C11'), 22.3 (d, J=43.5 Hz, C14'), 22.1 (d, J=12.5 Hz, C13').

In an embodiment, [5-(6-(3,4,5-trihydroxybenzamido) hexylamino) carbonylpentyl]triphenylphosphonium bromide (AntiOxBEN₃) was synthetized as follows: 1.0 g; 1.4 mmol was dissolved in 7.6 ml of anhydrous dichloromethane. The reaction mixture was stirred under argon and cooled at a temperature below −75° C. Boron tribromide (4.3 ml of 1 M solution in dichloromethane; 4.3 mmol) solution was added dropwise and the reaction was kept at −75° C. for 10 minutes. Once the addition was completed, the reaction was kept at −70° C. for 10 minutes and then allowed to warm to room temperature with continuous stirring for 12 hours. Thereafter, the reaction was finished by cautious addition of water (20 mL). After water removal, the resulting product was dissolved in methanol and dried over anhydrous Na₂SO₄, filtered, and the solvent evaporated. The residue was purified by flash chromatography (10% MeOH/CH₂Cl₂) and a yield of 55% was obtained.

In an embodiment, the structural characterization of the compound [5-(6-(3,4,5-trihydroxybenzamido)hexylamino) carbonylpentyl]triphenylphosphonium bromide (AntiOxBEN₃) was as follows: ¹H NMR (400 MHz, MeOD): δ=7.92-7.83 (3H, m, H4''), 7.82-7.70 (12H, m, 12H, m, H2'', H3'', H5'', H6''), 6.83 (2H, s, H2, H6), 3.43-3.34 (2H, m, H14'), 3.33-3.25 (2H, m, H2'), 3.14 (1H, t, J=6.9 Hz, H7'), 2.15 (1H, t, J=7.0 Hz, H10'), 1.72-1.28 (14H, m, H3', H4', H5', H6' H11', H12', H13'); ¹³C NMR (100 MHz, MeOD): δ=176.3 (C9), 170.5 (PhCOONH), 146.5 (C3, C5), 138.1 (C4), 136.1 (d, J=2.9 Hz, C4''), 134.7 (d, J$_{CP}$=10.0 Hz, C2'', C6''), 131.5 (d, J$_{CP}$=12.6 Hz, C3'', C4''), 125.4 (C1), 119.7 (d, J$_{CP}$=86.3 Hz, C1''), 107.8 (C2, C6), 40.8 (C2'), 40.5 (C7'), 36.2 (C10'), 30.9 (C3'), 30.8 (C6'), 30.2 (C4'), 29.9 (C5'), 27.4 (d, J$_{CP}$=2.5 Hz, C12'), 26.1 (C11'), 23.1 (d, J$_{CP}$=4.2 Hz, C13'), 22.6 (d, J$_{CP}$=51.3 Hz, C14'); ESI/MS m/z (%): 628 (M⁺+H—Br⁻, 38), 627 (M⁺—Br, 100), 556 (35), 547 (46); and ESI/HRMS m/z calc. for $C_{37}H_{44}N_2O_5P^+$ (M⁺—Br⁻): 627.2982; found 627.2970.

The radical scavenging activity of AntiOxClNs was evaluated by means of total antioxidant capacity assays based on DPPH., ABTS.+ and GO. radicals. All these methods involved the spectrophotometric measurement of the absorbance decrease resulting from radical (DPPH., ABTS.+ or GO.) deactivation with an antioxidant. The results were expressed in $IC_{50}$, which is defined as the minimum antioxidant concentration necessary to reduce the amount of radical by 50%. Antioxidant assays were performed in a multiplate reader (Powerwave XS Microplate Reader) from Bio Tech instruments.

In an embodiment, the DPPH radical scavenging activity was performed as follows: solutions of the test compounds with increasing concentrations (range between 0 μM and 500 μM) were prepared in ethanol. A DPPH ethanolic solution (6.85 mM) was also prepared and then diluted to reach the absorbance of 0.72±0.02 at 515 nm. Each compound solution (20 μL) was added to 180 μL of DPPH. solution in triplicate, and the absorbance at 515 nm was recorded minutely over 45 minutes. The percent inhibition of the radical was based on comparison between the blank (20 μL of ethanol and 180 μL of DPPH. solution), which corresponded to 100% of radical, and test compounds solutions. Dose-response curves were established for the determination of $IC_{50}$ values. Data are means±SEM of three independent experiments.

In an embodiment, the ABTS.+ scavenging activity was evaluated as follows: ethanolic solutions of the test compounds with increasing concentrations (range between 10 μM and 500 μM) were prepared. ABTS. radical cation solution was obtained by addition of 150 mM aqueous potassium persulfate solution (163 μL) to 10 mL of 7 mM aqueous ABTS solution followed by storage in the dark at room temperature for 16 h (2.45 mM final concentration). The solution was then diluted in ethanol to reach the absorbance of 0.72±0.02. After addition of the compound (20 μL), in triplicate, to ABTS.+ solution (180 μL) the spectrophotometric measurement was carried out each minute over 15 minutes. The percent inhibition of radical was based on comparison between the blank (20 μL of ethanol and 180 μL of ABTS.+ solution), which corresponds to 100% of radical, and test compounds solutions. Dose-response curves were established for the determination of IC50 values. Data are means±SEM of three independent experiments.

In an embodiment, the GO. scavenging activity was evaluated as follows: solutions of test compounds with concentrations from 10 μM to 100 μM were prepared in ethanol. An ethanolic solution of 5 mM GO. was prepared and diluted to reach the absorbance of 1.00±0.02 at 428 nm. The addition (20 μL) in triplicate of compound solution to GO. solution (180 μL) was followed by absorbance measurement at 428 nm over 30 minutes, in the dark, at room temperature. The percent inhibition of radical was based on comparison between the blank (20 μL of ethanol and 180 μL of GO. solution), which corresponds to 100% of radical, and test compounds solutions. Dose-response curves were established for the determination of IC50 values. Data are means±SEM of three independent experiments.

In an embodiment, the redox and lipophilic properties of AntiOxBENs were evaluated by electrochemical techniques.

In an embodiment, the electrochemical analytical data was obtained using a computer controlled potentiostat Autolab PGSTAT302N (Metrohm Autolab, Utrecht, Netherlands). Generally, cyclic voltammetry (CV) data was acquired at a scan rate of 50 mVs$^{-1}$. Differential pulse voltammetry (DPV) results were acquired at a step potential of 4 mV, pulse amplitude of 50 mV and scan rate of 8 mVs$^{-1}$.

The electrochemical signals were monitored by the General Purpose Electrochemical System (GPES) version 4.9, software package. All electrochemical experiments were performed at room temperature in an electrochemical cell that was placed in a Faraday cage in order to minimize the contribution of background noise to the analytical signal.

In an embodiment, the process of evaluation of AntiOxBENs redox properties was conducted as follows: stock solutions of each compound (10 mM) were prepared by dissolving the appropriate amount in ethanol. The voltammetric working solutions were prepared in the electrochemical cell, at a final concentration of 0.1 mM. The pH 0.7.4 supporting electrolyte was prepared by diluting 6.2 mL of 0.2 M dipotassium hydrogen phosphate and 43.8 mL of 0.2 M potassium dihydrogen phosphate to 100 mL. Voltammetric data was acquired in a three-electrode system consisting of a glassy carbon electrode (GCE, d=2 mm) as working electrode, a counter electrode of platinum wire and a saturated Ag/AgCl reference electrode. In an embodiment, the evaluation of AntiOxBENs lipophilic properties was performed as follows: the electrochemical cell was a four-electrode system with arrays of micro liquid-liquid interfaces (μITIES) containing two Ag/AgCl reference electrodes and two counter electrodes of Pt, one in each phase. The microporous membrane was sealed with a fluorosilicone sealant (Dow Corning 730) onto a glass cylinder which was filled with 4.0 mL of the aqueous phase, where the aliquots of AntiOxBENs solutions were added. The membrane was then immersed into the organic phase contained in the cell. The organic phase reference solution (a 2 mM BTPPACl+2 mM NaCl aqueous solution) was mechanically stabilized The aqueous supporting electrolyte solution was a Tris-HCl buffer 10 mM pH 7.0.

In an embodiment, AntiOxBENs iron chelating properties were evaluated by the spectrophotometric ferrozine method performed in a multiplate reader (Powerwave XS Microplate Reader) of Bio-Tech instruments.

In an embodiment, the AntiOxBENs iron chelating properties were evaluated as follows: in each well, a solution of the test compound (100 μM) and ammonium iron (II) sulphate in ammonium acetate (20 μM) were added, incubated for 10 min and the absorbance was read at 562 nm. Then, a freshly prepared solution of ferrozine (5 mM) was added to each well (96 μM final concentration). After a new incubation at 37° C. for 10 min period, the absorbance of [Fe(ferrozine)3]$^{2+}$ complex was measured at 562 nm. Blank wells were run using DMSO instead of the test compounds. EDTA was used as a reference. All compounds were tested at a final concentration of 100 μM. The absorbance of the first reading was subtracted to the final values to abolish any absorbance due to the test compounds. Data are means±SEM of three independent experiments and are expressed as % of Fe(II) chelation (EDTA=100%).

In an embodiment, the evaluation of AntiOxBENs functional mitochondrial toxicity profile was performed in rat liver mitochondria (RLM). RLM were prepared by tissue homogenization followed by differential centrifugations in ice-cold buffer containing 250 mM sucrose, 10 mM HEPES (pH 7.4), 1 mM EGTA, and 0.1% fat free bovine serum albumin. After obtaining a crude mitochondrial preparation, pellets were washed twice and resuspended in washing buffer (250 mM sucrose and 10 mM HEPES, pH 7.4). The protein concentration was determined by the biuret assay using BSA as a standard.

In an embodiment, the mitochondrial AntiOxBENs uptake was evaluated.

In an embodiment, the AntiOxBENs mitochondria uptake by energized RLM was evaluated as follows: RLM (0.5 mg protein/mL) were incubated with AntiOxBENs at 37° C. under constant stirring in 1 mL of KCl medium (120 mM KCl, 10 mM HEPES, pH 7.2 and 1 mM EGTA). Five sequential 1 µM additions of each AntiOxBENs were performed to calibrate the electrode response in the presence of rotenone (1.5 µM). Then, succinate (10 mM) was added to generate 64. Valinomicin (0.2 µg/mL) was added at the end of the assay to dissipate $\Delta\psi$. The measurements were performed with an ion-selective electrode, which measure the distribution of tetraphenylphosphonium cation (TPP+) and Ag/AgCl2 electrode as reference. The mitochondrial accumulation ratio was calculated by the disappearance of AntiOxBENs from extra- to intramitochondrial medium assuming an intramitochondrial volume of 0.5 µL/mg protein and a binding correction for the mitochondrial uptake of TPP compounds.

The outcome of AntiOxBENs on RLM lipid peroxidation was evaluated. Two different methods have been used.

In an embodiment, the effect of AntiOxBENs on RLM lipid peroxidation was measured by thiobarbituric acid reactive species (TBARS) assay as follows: RLM (2 mg protein/ml) were incubated in 0.8 mL medium containing 100 mM KCl, 10 mM Tris-HCl and pH 7.6, at 37° C., supplemented with 5 mM glutamate/2.5 mM malate as substrate. RLM were incubated for 5 min period with each AntiOxBENs (5 µM) and then mitochondria were exposed to oxidative stress condition by the addition of 100 µM $FeSO_4$/500 µM $H_2O_2$/5 mM ascorbate for 15 min at 37° C. After exposure to oxidative stress, 60 µL of 2% (v/v) butylated hydroxytoluene in DMSO was added, followed by 200 µL of 35% (v/v) perchloric acid and 200 µL of 1% (w/v) thiobarbituric acid. Samples were then incubated for 15 min at 100° C., allowed to cool down and the supernatant transferred to a glass tube. After addition of 2 mL MiliQ water and 2 mL butan 1-ol, samples were vigorously vortexed for few seconds. The two phases were allowed to separate. The fluorescence of aliquots (250 µL) of the organic layer was analyzed in a plate reader ($\lambda Ex$=515 nm; $\lambda Em$=553 nm) for TBARS. The TBARS background production in RLM energized with glutamate/malate was found to be negligible. Data are means±SEM of three independent experiments and are expressed as % of control (control=100%).

In an embodiment, the effect of AntiOxBENs on RLM lipid peroxidation was measured by a second methodology as follows: the oxygen consumption of 2 mg RLM, in a total volume of 1 mL of a reaction medium consisting of 100 mM KCl, 10 mM Tris-HCl and pH 7.6, using glutamate/malate (5 mM/2.5 mM) as respiratory substrate, was monitored at 37° C. with a Clark oxygen electrode. RLM were incubated for 5 min period with each AntiOxBENs (5 µM) and then lipid peroxidation process started by adding 1 mM ADP and 0.1 mM $FeSO_4$ (final concentrations). The saturated concentration of $O_2$ in the incubation medium was assumed to be 217 µM at 37° C. Time-dependent changes on oxygen consumption resulting from peroxidation of RLM membranes by a pro-oxidant pair (1 mM ADP/0.1 mM $FeSO_4$) were recorded. The traces are means±SEM recording from six independent experiments. The time lag-phase associated with the slower oxygen consumption that followed the addition of ADP/$Fe^{2+}$ was used to measure the effectiveness of AntiOxBENs to prevent lipid peroxidation. Data are means±SEM from six independent experiments and are expressed as % of control (control=100%).

In an embodiment, the effect of AntiOxBENs on mitochondrial permeability transition pore opening was evaluated.

In an embodiment, the effect of AntiOxBENs on mitochondrial permeability transition pore opening were measured as follows: mitochondrial swelling was estimated by measuring the alterations of light scattered from a mitochondrial suspension, as monitored spectrophotometrically at 540 nm. Increasing concentrations of AntiOxBENs (2.5-10 µM) were added to the reaction medium (200 mM sucrose, 1 mM $KH_2PO_4$, 10 mM Tris (pH 7.4), 5 mM succinate and 10 µM EGTA supplemented with 1.5 µM rotenone), in the presence of RLM (1 mg), and allowed to incubate for a 5 min period before the assay. The experiments were initiated by the addition of a suitable concentration of $Ca^{2+}$ (15-50 µM), titrated every day. Cyclosporin A (CsA), a PTP desensitizer, was added to demonstrate mPTP opening. The reaction was stirred continuously and the temperature maintained at 37° C. Data are means±SEM of three independent experiments and are expressed as absorbance at 540 nm.

In an embodiment, the effect of AntiOxClNs on mitochondrial respiration was evaluated.

In an embodiment, the evaluation of AntiOxBENs effect on mitochondrial respiration was performed as follows: the respiration of isolated RLM was evaluated polarographically with a Clark-type oxygen electrode, connected to a suitable recorder in a 1 mL thermostated water-jacketed chamber with magnetic stirring, at 37° C. The standard respiratory medium consisted of 130 mM sucrose, 50 mM KCl, 5 mM $KH_2PO_4$, 5 mM HEPES (pH 7.3) and 10 µM EGTA. Increasing concentrations of AntiOxBENs (2.5-10 µM) were added to the reaction medium containing respiratory substrates glutamate/malate (10 mM and 5 mM respectively) or succinate (5 mM) and RLM (1 mg) and allowed to incubate for a 5 min period prior to the assay. State 2 was considered as the respiration during the 5 min incubation time with AntiOxBENs. To induce state 3 respiration, 125 nmol ADP (using glutamate/malate) or 75 nmol ADP (using succinate) was added. State 4 was determined after ADP phosphorylation finished. Subsequent addition of oligomycin (2 µg/ml) inhibited ATPsynthase and originated the oligomycin-inhibition respiration state. Finally, 1 µM FCCP was added to induce uncoupled respiration. The RCR was of 7.3±0.6 and 4.1±0.3 for the control experiments, with glutamate-malate or succinate as respiratory substrates, respectively. The ADP/O index was 2.6±0.1 and 1.5±0.1 with the same respiratory substrates, respectively. Data are means are means±SEM of seven independent experiments.

In an embodiment, the effect of AntiOxBENs on transmembrane electric potential ($\Delta\psi$) was evaluated.

In an embodiment, the evaluation of AntiOxBENs effect on mitochondrial transmembrane electric potential ($\Delta\psi$) was performed as follows: the mitochondrial transmembrane electric potential ($\Delta\psi$) was estimated through the evaluation of fluorescence changes of safranine (5 µM) and was recorded on a spectrofluorometer operating at excitation and emission wavelengths of 495 and 586 nm, with a slit width of 5 nm. Increasing concentrations of AntiOxBENs (2.5-10 µM) were added to the reaction medium (200 mM sucrose, 1 mM $KH_2PO^4$, 10 mM Tris (pH 7.4) and 10 µM EGTA) containing respiratory substrates glutamate/malate (5 mM and 2.5 mM respectively) or succinate (5 mM) and RLM (0.5 mg in 2 mL final volume) and allowed to incubate for a 5 min period prior to initiate the assay, at 25° C. In this assay, safranine (5 µM) and ADP (25 nmol) were used to initiate the assay and to induce depolarization, respectively. Then, 1 µM FCCP was added at the end of all experiments to depolarize mitochondria. Δψ was calculated using a calibration curve obtained when RLM were incubated in a K$^+$-free reaction medium containing 200 mM sucrose, 1 mM NaH$_2$PO$_4$, 10 mM Tris (pH 7.4) and 10 μM EGTA, supplemented with 0.4 μg valinomicin. The extension of fluorescence changes of safranine induced by Δψ was found to be similar in the standard and K$^+$-free medium. "Repolarization" corresponded to the recovery of membrane potential after the complete phosphorylation of ADP added. Lag phase reflected the time required to phosphorylate the added ADP. Isolated RLM developed a Δψ≈226 mV and Δψ≈202 mV (negative inside) when glutamate/malate or succinate were used, respectively. Data are means±SEM of five independent experiments.

In an embodiment, the cytotoxicity profile of Anti-OxBENs was evaluated in human hepatocellular carcinoma HepG2 cells. Human hepatocellular carcinoma HepG2 cells were cultured in high-glucose medium composed by Dulbecco's modified Eagle's medium (DMEM; D5648) supplemented with sodium pyruvate (0.11 g/L), sodium bicarbonate (1.8 g/L) and 10% fetal bovine serum (FBS) and 1% of antibiotic penicillin-streptomycin 100× solution. Cells were maintained at 37° C. in a humidified incubator with 5% CO$_2$. HepG2 cells were seeded at density of 4×10$^4$ cells/mL and grown for 24 hours before treatment.

In an embodiment the cytotoxicity screening was performed as follows: cells were placed on 48-well plate (2×10$^4$ cells/500 μL) and then were incubated during 48 hour with AntiOxBENs concentrations ranging 25 μM to 500 μM. After incubation, sulforhodamine B (SRB) assay was used for cell density determination based on the measurement of cellular protein content. Briefly, after incubation, the medium was removed and wells rinsed with PBS (1λ). Cells were fixed by adding 1% acetic acid in 100% methanol for at least 2 hours at −20° C. Later, the fixation solution was discarded and the plates were dried in an oven at 37° C. Two hundred and fifty microliters of 0.5% SRB in 1% acetic acid solution was added and incubated at 37° C. for 1 h. The wells were then washed with 1% acetic acid in water and dried. Then, 500 μl of Tris (pH 10) was added and the plates were stirred for 15 min. Finally, 200 μl of each supernatant was transferred in 96-well plates and optical density was measured at 540 nm. Data are means±SEM of four independent experiments and the results are expressed as percentage of control (control=100%), which represents the cell density without any treatment in the respective time point.

In an embodiment, all the biological data was analyzed as follows: in GraphPad Prism 5.0 software (GraphPad Software, Inc.), with all results being expressed as means±SEM for the number of experiments indicated. Data were analyzed by the student's t test for comparison of two means, and one-way ANOVA with Dunnet multiple comparison post-test. The last test was used to compare more than two groups with one independent variable. Significance was accepted with *P<0.05, P<0.01, *P<0.0005, ****P<0.0001.

The disclosure should not be seen in any way restricted to the embodiments described and a person with ordinary skill in the art will foresee many possibilities to modifications thereof.

The above described embodiments are combinable. The following claims further set out particular embodiments of the disclosure.

REFERENCES

1. Pagano, G., Talamanca, A. A., Castello, G., Cordero, M. D., d'Ischia, M., Gadaleta, M. N., Pallardo, F. V., Petrovic, S., Tiano, L., and Zatterale, A. (2014) Oxidative stress and mitochondrial dysfunction across broad-ranging pathologies: toward mitochondria-targeted clinical strategies. *Oxidative medicine and cellular longevity,* 2014, 541230.
2. Smith, R. A., Hartley, R. C., Cocheme, H. M., and Murphy, M. P. (2012) Mitochondrial pharmacology. *Trends in pharmacological sciences,* 33, 341-352.
3. Teixeira, J., Soares, P., Benfeito, S., Gaspar, A., Garrido, J., Murphy, M. P., and Borges, F. (2012) Rational discovery and development of a mitochondria-targeted antioxidant based on cinnamic acid scaffold. *Free radical research,* 46, 600-611.
4. Reily, C., Mitchell, T., Chacko, B. K., Benavides, G., Murphy, M. P., and Darley-Usmar, V. (2013) Mitochondrially targeted compounds and their impact on cellular bioenergetics. *Redox biology,* 1, 86-93.
5. Trnka, J., Elkalaf, M., and Andel, M. (2015) Lipophilic triphenylphosphonium cations inhibit mitochondrial electron transport chain and induce mitochondrial proton leak. *PloS one,* 10, e0121837.

The invention claimed is:

1. A compound of formula I

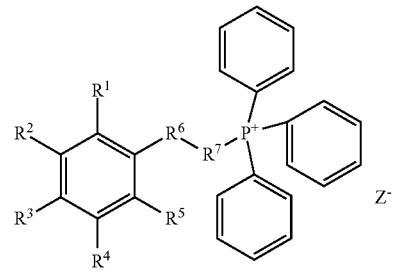

or a salt, tautomer, or stereoisomer thereof,
wherein
R', R$^2$, R$^3$, R$^4$, R$^5$, R$^6$ and R$^7$ are independently selected from each other;
R', R$^2$, R$^3$, R$^4$ and R$^5$ are selected from H, halogen, hydroxyl, methyl, methoxyl, amino, carboxylic acid, or nitro group;
R$^6$ is a secondary amide or tertiary amide;
R$^7$ is an alkyl chain, an alkenyl chain, an alkynyl chain, a substituted aryl, or a secondary amide;
Z$^-$ is an acceptable anion; and
wherein the alkyl chain, the alkenyl chain or the alkynyl chain is a C$_5$-C$_{30}$ chain.

2. The compound of claim 1, wherein the compound has the following formula:

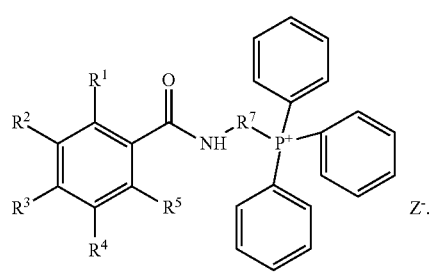

3. The compound of claim 1, wherein the compound has the following formula:

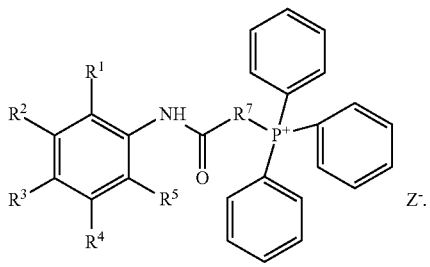

4. The compound of claim 1, wherein
R$^7$ is a secondary amide of R$^8$-(C=O)NH-R$^9$ amide,
R$^8$ and R$^9$ are independently selected from each other and R$^8$ and R$^9$ are an alkyl chain, an alkenyl chain, an alkynyl chain or a substituted aryl.

5. The compound of claim 1, wherein the substituted aryl is an alkane-aryl substituted, alkene-aryl substituted, or alkyne-aryl substituted.

6. The compound of claim 1, wherein the alkyl chain, the alkenyl chain or the alkynyl chain is a C$_6$-C$_{14}$ chain.

7. The compound of claim 1, wherein R$^1$ and R$^5$ are H.

8. The compound of claim 1, wherein R$^2$ and R$^3$ are OH.

9. The compound of claim 1, wherein R$^4$ is H or OH.

10. The compound of claim 1, wherein R$^7$ is a C$_6$ alkyl chain.

11. The compound of claim 4 wherein R$^8$ and R$^9$ are independently of each other a C$_5$ alkyl chain or a C$_6$ alkyl chain.

12. The compound of claim 1, wherein the compound is 6-(3,4-dihydroxybenzamido)hexyltriphenylphosphonium bromide.

13. The compound of claim 1, wherein the compound is 6-(3,4,5-trihydroxybenzamido)hexyltriphenylphosphonium bromide.

14. The compound of claim 1, wherein the compound is 5-(6-(3,4,5-trihydroxybenzamido)hexylamino) carbonyl-pentyl]triphenylphosphonium bromide.

15. A composition comprising the compound of claim 1 and a pharmaceutically acceptable carrier, adjuvant, excipient, or diluent or mixtures thereof.

16. The composition of claim 15, wherein the pharmaceutically acceptable carrier is saline, gum acacia, gelatin, starch paste, talc, keratin, colloidal silica, urea or mixtures thereof.

17. The composition of claim 15, wherein the adjuvant is oil-in-water emulsion adjuvant, aluminium adjuvant, a TLR-4 ligand, a saponin, or mixtures thereof.

18. The composition of claim 15, wherein the excipient is glucose, lactose, sucrose, glycerol monostearate, sodium chloride, glycerol, propylene, glycol, water, ethanol or mixtures thereof.

* * * * *